(12) United States Patent
Umemoto

(10) Patent No.: US 9,765,353 B2
(45) Date of Patent: Sep. 19, 2017

(54) PLANT HAVING SUPPRESSED EXPRESSION OF GLYCOALKALOID BIOSYNTHETIC ENZYME GENE OR ALTERED ACTIVITY OF THE ENZYME

(71) Applicant: KIRIN HOLDINGS KABUSHIKI KAISHA, Nakano-ku, Tokyo (JP)

(72) Inventor: Naoyuki Umemoto, Nakano-ku (JP)

(73) Assignee: KIRIN HOLDINGS KABUSHIKI KAISHA, Nakano-ku, Tokyo (JP)

( * ) Notice: Subject to any disclaimer, the term of this patent is extended or adjusted under 35 U.S.C. 154(b) by 119 days.

(21) Appl. No.: 14/382,913

(22) PCT Filed: Mar. 6, 2013

(86) PCT No.: PCT/JP2013/056163
§ 371 (c)(1),
(2) Date: Sep. 4, 2014

(87) PCT Pub. No.: WO2013/133330
PCT Pub. Date: Sep. 12, 2013

(65) Prior Publication Data
US 2015/0074857 A1  Mar. 12, 2015

(30) Foreign Application Priority Data
Mar. 7, 2012 (JP) ................................ 2012-051011

(51) Int. Cl.
| C12N 15/82 | (2006.01) |
| A01H 1/04 | (2006.01) |
| A01H 5/04 | (2006.01) |
| C07K 14/415 | (2006.01) |
| C12N 9/02 | (2006.01) |
| C12Q 1/68 | (2006.01) |
| A01H 1/02 | (2006.01) |
| A01H 5/06 | (2006.01) |

(52) U.S. Cl.
CPC .......... *C12N 15/8243* (2013.01); *A01H 1/02* (2013.01); *A01H 1/04* (2013.01); *A01H 5/04* (2013.01); *A01H 5/06* (2013.01); *C07K 14/415* (2013.01); *C12N 9/0004* (2013.01); *C12Q 1/6895* (2013.01); *C12Q 2600/13* (2013.01); *C12Q 2600/156* (2013.01)

(58) Field of Classification Search
CPC .................................................. C12N 15/8243
See application file for complete search history.

(56) References Cited

U.S. PATENT DOCUMENTS

| 2012/0159676 A1 | 6/2012 | Umemoto et al. |
| 2013/0167271 A1 | 6/2013 | Umemoto et al. |

FOREIGN PATENT DOCUMENTS

| WO | 2011/025011 A1 | 3/2011 | |
| WO | 2012/029804 A1 | 3/2012 | |
| WO | WO 2012/095843 | * 7/2012 | ......... C12N 15/8218 |

OTHER PUBLICATIONS

Ginzburg, I., et al. Potato Research (2009) vol. 52; pp. 1-15.*
Eckart Eich, "Solanaceae and Convolvulaceae: Secondary Metabolites" Biosynthesis, Chemotaxonomy, Biological and Economic Significance (A Handbook), Springer, 2008, pp. 398-461.
Idit Ginzberg et al., "Potato Steroidal Glycoalkaloids: Biosynthesis and Genetic Manipulation", Potato Research, 2009, pp. 1-15, vol. 52.
Toshihiro Nohara et al., "The Tomato Saponin, Esculeoside A", J. Nat. Prod., 2010, pp. 1734-1741, vol. 73.
Eckart Eich, "Solanaceae and Convolvulaceae: Secondary Metabolites" Biosynthesis, Chemotaxonomy, Biological and Economic Significance (A Handbook), Springer, 2008, pp. 368-373.
Ko Kaneko et al., "Structure of Barogenin From Solanum Tuberosum", Phytochemistry, 1977, pp. 791-793, vol. 16.
Kent. F. McCue et al., "Metabolic compensation of steroidal glycoalkaloid biosynthesis in transgenic potato tubers: using reverse genetics to confirm the in vivo enzyme function of a steroidal alkaloid galactosyltransferase", Plant Science, 2005, pp. 267-273, vol. 168.
Kent F. McCue et al., "The primary in vivo steroidal alkaloid glucosyltransferase from potato", Phytochemistry, 2006, pp. 1590-1597, vol. 67.
Kent F. McCue et al., "Potato glycosterol rhamnosyltransferase, the terminal step in triose side-chain biosynthesis", Phytochemistry, 2007, pp. 327-334, vol. 68.
Lisa Arnqvist et al., "Reduction of Cholesterol and Glycoalkaloid Levels in Transgenic Potato Plants by Overexpression of a Type 1 Sterol Methyltransferase cDNA", Plant Physiol., 2003, pp. 1792-1799, vol. 131.
Erich Heftmann, "Biogenesis of Steroids in Solanaceae", Phytochemistry, 1983, pp. 1843-1860, vol. 22, No. 9.
International Search Report for PCT/JP2013/056163 dated Apr. 9, 2013.

* cited by examiner

*Primary Examiner* — Russell Kallis
(74) *Attorney, Agent, or Firm* — Sughrue Mion, PLLC

(57) ABSTRACT

Provided are the DNA of a glycoalkaloid biosynthetic enzyme of solanaceous plants (Solanaceae) such as potato, solanaceous plants producing no glycoalkaloids, and a method of producing a cultivar with a reduced risk of accumulating glycoalkaloids, which involves crossing plants in which the expression of an oxidase gene involved in glycoalkaloid biosynthesis is suppressed or the activity of the enzyme is lowered, as mother plants, and screening progeny resulting from the crossing.

1 Claim, 11 Drawing Sheets

Fig. 1-1

```
1st Nucleotide Sequence
  File Name      : potato E
  Sequence Size  : 1461
2nd Nucleotide Sequence
  File Name      : tomato E
  Sequence Size  : 1461
[94.589% / 1460 bp]    INT/OPT.Score : <   5366/  5366 >
     1' ATGGATTTCT ACAATTTAGC CTTATTCTTC ATAGCTTTAG TAATTGGGAT TTTCACATTT
        ********** ********** ***  ***** ********** **  **** ** **********
     1" ATGGATTTCT ACAATTTAGC CTTGTTCTTC ATAGCTTTAA TACTTGGAAT TTTCACATTT 61' TATGCTATAT TAATGAGAAT TAATGGTTGG TATTATGCAA TCAAATTTTG TTCAAAGAAA
        ***  * ******** ****** ****** ****** **  *
    61" TATGCCATAT TAATGAGAAT AAATGGTTGG TATTATGCAA TCAAATTTTG TTCAAACAAA 121' TATAACATCC CTCTAGGTTA TATGGGTTTG CCATATTTTG CAACACACT TTCTTACTTC
        ********** *     *** ****** ******** * ******* ********
   121" TATAACATCC CAAATGGTTA TATGGGTTTG CCATATTTTG GTAACACACT TTCTTACTTC 181' AAATCTACCA TTTGTGGTGA TCCAAATTCA TTCCTTGATT TCTTTGCTAC TAGGTTTGGG
        *  * * * ****** **  * * ** ****** *******
   181" AAAGCTTCAA TGTGTGGTGA TCCAAAATCA TTCATTGATT TCTTTGCTAC TAGGTTTGGA 241' ACAGGAGGAA TGTATAGGGC ATACATATTT GGGAAGCCAA CAATTATGGT GACAAAGCCA
        ******  ****** ****** ****** ****** ********
   241" GAAGGAGGAA TGTATAGGGC ATACATATTT GGGAAGCCAA CAATTATGGT GACAAAGCCA 301' GAAATAATTA GAAAAGTTTT GATGGATGAA GAATATCTTG AAAGAGGTTT GCCTAATTAT
        ******** ****** ******  ***** ****** ********
   301" GAAATAATTA GAAAAGTTTT GATGGATGAA GAGTATCTTG AAAGAGGTTT GCCTAATTAT 361' ATGAAAAAAT TAATTGGATT AACAACTTCG ATTGAAGAAG ATAAATATTT TCGTCGATTA
        ******** ****** ******  ******* * *******  ***
   361" ATGAAAAAAT TAATTGGATT AACAACTTCG ATAGAAGAAG ACAAATATTT TCGTAGATTA 421' ACATCTCCAG TAAAAAGTCA TGGATTATTA TCCGATTATT TTGATTATAT CGATAAAACT
        *** * ** ****** ******  ******* * ****** ********
   421" ACAGCACCAG TAAAAAGTCA TGGATTATTA TCTGATTATT TCGATTATAT CGATAAAACT 481' GTGAGCACTA CATTAGAGAA ATACGCTACT ACGGAAGAAC CTATTGAGTT TCTCCATAAG
        ***  * ******** ****** ******  ***** * *****
   481" GTGAGTTCTA CATTAGAGAA ATACGCTACT ACGGAAGAAC CTGTTGAGTT TCTTCATAAA
```

Fig. 1-2

```
541'  ATGCACAGGC TTGCATTTGA GGTGTTTATG AGACTTCTTA TTGGTGATGA GGTTAATCAA
      ******* ** ** * ***** ********** ****** * * **********   *********
541"  ATGCACAAGC TTACGTTTGA GGTGTTTATG AGACTTTTAA TTGGTGATGA AGTTAATCAA

601'  GAATTTTTTG ATCAAATGTT TGTGGAGATT ACTGCTGTAA TTAGTGCTGT TCACAACTTG
      ***** **** ** ******* ** ******* ********** ****** *** ****** ***
601"  GAATTATTTG ATGAAATGTT TGAGGAGATT ACTGCTGTAA TTAGTGGTGT TCACAATTTG

661'  CCAATTAATC TCCCAGGATT TCCTTATCAT AAGGGACTCA AGGCTCGAAA AGTACTAGGA
      ********** ********** * ******** ********** ********** **********
661"  CCAATTAATC TCCCAGGATT TGCTTATCAT AAGGGACTCA AGGCTCGAAA AGTACTAGGA

721'  GGGATATTTC AAAAACTAAT AGATGAAAGA AGAGAAGCCA TGAAGGATGG AAAATCAATG
      * * ***** ***** ****    ********* ********** ********** **********
721"  GAGGTATTTA AAAAATTAAT TGATGAAAGA AGAGAAGCCA TGAAGGATGG AAAATCAATG

781'  CCAAGGGCAA ACATAATTGA TATGTTGTTA TCAAACACTA ATCAAGATTA TGAAGACAAT
      **** ***** ********** ********** *******  * ********** *****   **
781"  CCAAAGGCAA ACATAATTGA TATGTTGTTA TCAAACAACA ATCAAGATTA TGAAGCAAAC

841'  ATATTGAGTG ACAAGAAGAT CGTTGAAATC CTAGTTTTGT TTTCATTTGC TGGTTTTGAA
      ** ******* ********** * ********* ********** ********** **********
841"  ATGTTGAGTG ACAAGAAGAT CATTGAAATC CTAGTTTTGT TTTCATTTGC TGGTTTTGAA

901'  CCTGTTGCTC TTATGTCTGT CAAGGCAATT TTTCACTTGC AAAAGCATCC CCATTTCTTG
      ********** ********** ********** ** ***** * **** *****   *********
901"  CCTGTTGCTC TTATGTCTGT CAAGGCAATT TTCCACTTAC AAAAACATCC ACATTTCTTG

961'  GAGAAAGCCA AAGAGGAACA AGAGGAAATA GTAAAGAGAA GAGCATCTTC AAATGCTGGA
      ** ******* ********** ********** ********** ********** **********
961"  GAAAAAGCCA AAGAGGAACA AGAGGAAATA GTAAAGAGAA GAGCATCTTC AAATGCTGGA

1021' CTTAGTTTTG ATGAGATTAG GCAAATGACG TTTGTTAGTA AGGTAATTAA TGAAACGTTA
      ********** **** *****  ********    ********** ** ******* **********
1021" CTTAGTTTTG ATGAAATTAG ACAAATGACA TTTGTTAGTA AGATAATTAA TGAAACGTTA

1081' CGTATTGCTA CTGATCAAAC GGTATTCCTT AGAGACACAA GTACTACTTT TAACATAAAT
      ***** **** *******  * ********** ********** ********** **********
1081" CGTATAGCTA CTGATCAGTC GGTATTCCTT AGAGACACAA GTACTACTTT TAACATAAAT

1141' GGGTACACCA TACCCAAAGG GTGGAAGTTT TTTGCAGTTG TATGGAATAT TCATATGAAT
      ********** ********** ********** ********** ********** **********
1141" GGGTACACCA TACCCAAAGG GTGGAAGTTT TTTGCAGTTG TATGGAATAT TCATATGAAT
```

Fig. 1-3

```
1201' CCTGATGTTT ATGTTCAGCC TAAGGAATTT AATCCTTCAA GATGGGATGA TATTGAAACT
      ********** *******  **  ********** ********  *  ********** **********
1201" CCTGATGTTT ATGTTCAACC TAAGGAATTT AATCCTTCGA GATGGGATGA TATTGAAACT

1261' AAGCCAGGCA TTTTTCTTCC ATTTTCAATG GGCCCCAAAT CATGCCCAGG ATCCAATCTG
      ********** *******  **   ********* ********** ********** *******  **
1261" AAGCCAGGCA TTTTTCTACC TTTTTCAATG GGCCCCAAAT CATGCCCAGG ATCCAATTTG

1321' GCCAAGCTTC AAATTTCAGT AATTCTTCAT TATTATCTTC TTCACTACAG GGTTGAGCAA
      ********** ********** ********** ********** ********** **********
1321" GCCAAGCTTC AAATTTCAGT AATTCTTCAT TATTATCTTC TTCACTACAG GGTTGAGCAA

1381' ATTAATCCAG AGGCTAGATG TTATCCTCCT GAAAATTGTC TTGTGAAATT CAAGAAGCTC
      ********** ********** ********** ********** ********** *********
1381" ATTAATCCAG AGGCTAGATG TTATCCTCCT GAAAATTGTC TTGTGAAATT CAAGAAGCTA

1441' TCAATCTCTA GTGATGGTAA C (SEQ ID NO:2)
      **  ******* **  *******
1441" TCGATCTCTA GTAATGGTAA T (SEQ ID NO:4)
```

1: Non-transformant
2: Non-transformant
3: pKT230 Transformant #2
4: pKT230 Transformant #8
5: pKT230 Transformant #17
6: pKT230 Transformant #22
7: pKT230 Transformant #27
8: pKT230 Transformant #29

1: FTT1
2: FTT2
3: FTT3
4: FTT4
5: FTT5
6: FTT6
7: FTT7
8: FTT8
9: FTT10
10: FTT11
11: Sassy
12: FTT16

1: FTT1
2: FTT16
3: Sassy

SEQUENCE LISTING

```
<160> NUMBER OF SEQ ID NOS: 31

<210> SEQ ID NO 1
<211> LENGTH: 487
<212> TYPE: PRT
<213> ORGANISM: Solanum tuberosum
```

<400> SEQUENCE: 1

```
Met Asp Phe Tyr Asn Leu Ala Leu Phe Ile Ala Leu Val Ile Gly
1               5                   10                  15

Ile Phe Thr Phe Tyr Ala Ile Leu Met Arg Ile Asn Gly Trp Tyr Tyr
            20                  25                  30

Ala Ile Lys Phe Cys Ser Lys Lys Tyr Asn Ile Pro Leu Gly Tyr Met
            35                  40                  45

Gly Leu Pro Tyr Phe Gly Asn Thr Leu Ser Tyr Phe Lys Ser Thr Ile
        50                  55                  60

Cys Gly Asp Pro Asn Ser Phe Leu Asp Phe Ala Thr Arg Phe Gly
65                  70                  75                  80

Thr Gly Gly Met Tyr Arg Ala Tyr Ile Phe Gly Lys Pro Thr Ile Met
                85                  90                  95

Val Thr Lys Pro Glu Ile Ile Arg Lys Val Leu Met Asp Glu Glu Tyr
            100                 105                 110

Leu Glu Arg Gly Leu Pro Asn Tyr Met Lys Lys Leu Ile Gly Leu Thr
            115                 120                 125

Thr Ser Ile Glu Glu Asp Lys Tyr Phe Arg Arg Leu Thr Ser Pro Val
130                 135                 140

Lys Ser His Gly Leu Leu Ser Asp Tyr Phe Asp Tyr Ile Asp Lys Thr
145                 150                 155                 160

Val Ser Thr Thr Leu Glu Lys Tyr Ala Thr Thr Glu Glu Pro Ile Glu
                165                 170                 175

Phe Leu His Lys Met His Arg Leu Ala Phe Glu Val Phe Met Arg Leu
            180                 185                 190

Leu Ile Gly Asp Glu Val Asn Gln Glu Phe Phe Asp Gln Met Phe Val
            195                 200                 205

Glu Ile Thr Ala Val Ile Ser Ala Val His Asn Leu Pro Ile Asn Leu
210                 215                 220

Pro Gly Phe Pro Tyr His Lys Gly Leu Lys Ala Arg Lys Val Leu Gly
225                 230                 235                 240

Gly Ile Phe Gln Lys Leu Ile Asp Glu Arg Arg Glu Ala Met Lys Asp
                245                 250                 255

Gly Lys Ser Met Pro Arg Ala Asn Ile Ile Asp Met Leu Leu Ser Asn
            260                 265                 270

Thr Asn Gln Asp Tyr Glu Asp Asn Ile Leu Ser Asp Lys Lys Ile Val
            275                 280                 285

Glu Ile Leu Val Leu Phe Ser Phe Ala Gly Phe Glu Pro Val Ala Leu
290                 295                 300

Met Ser Val Lys Ala Ile Phe His Leu Gln Lys His Pro His Phe Leu
305                 310                 315                 320

Glu Lys Ala Lys Glu Glu Gln Glu Ile Val Lys Arg Arg Ala Ser
                325                 330                 335

Ser Asn Ala Gly Leu Ser Phe Asp Glu Ile Arg Gln Met Thr Phe Val
            340                 345                 350

Ser Lys Val Ile Asn Glu Thr Leu Arg Ile Ala Thr Asp Gln Thr Val
            355                 360                 365

Phe Leu Arg Asp Thr Ser Thr Thr Phe Asn Ile Asn Gly Tyr Thr Ile
370                 375                 380

Pro Lys Gly Trp Lys Phe Phe Ala Val Val Trp Asn Ile His Met Asn
385                 390                 395                 400
```

```
Pro Asp Val Tyr Val Gln Pro Lys Glu Phe Asn Pro Ser Arg Trp Asp
            405                 410                 415

Asp Ile Glu Thr Lys Pro Gly Ile Phe Leu Pro Phe Ser Met Gly Pro
            420                 425                 430

Lys Ser Cys Pro Gly Ser Asn Leu Ala Lys Leu Gln Ile Ser Val Ile
            435                 440                 445

Leu His Tyr Tyr Leu Leu His Tyr Arg Val Glu Gln Ile Asn Pro Glu
            450                 455                 460

Ala Arg Cys Tyr Pro Pro Glu Asn Cys Leu Val Lys Phe Lys Lys Leu
465                 470                 475                 480

Ser Ile Ser Ser Asp Gly Asn
            485
```

<210> SEQ ID NO 2
<211> LENGTH: 1461
<212> TYPE: DNA
<213> ORGANISM: Solanum tuberosum

<400> SEQUENCE: 2

| | | | | | | |
|---|---|---|---|---|---|---|
| atggatttct | acaatttagc | cttattcttc | atagctttag | taattgggat | tttcacattt |   60 |
| tatgctatat | taatgagaat | taatggttgg | tattatgcaa | tcaaattttg | ttcaaagaaa |  120 |
| tataacatcc | ctctaggtta | tatgggtttg | ccatattttg | caacacact | ttcttacttc |  180 |
| aaatctacca | tttgtggtga | tccaaattca | ttccttgatt | tctttgctac | taggtttggg |  240 |
| acaggaggaa | tgtataggc | atacatattt | gggaagccaa | caattatggt | gacaaagcca |  300 |
| gaaataatta | gaaagtttt | gatggatgaa | gaatatcttg | aaagaggttt | gcctaattat |  360 |
| atgaaaaaat | taattggatt | aacaacttcg | attgaagaag | ataaatattt | cgtcgatta |  420 |
| acatctccag | taaaaagtca | tggattatta | tccgattatt | ttgattatat | cgataaaact |  480 |
| gtgagcacta | cattagagaa | atacgctact | acggaagaac | ctattgagtt | tctccataag |  540 |
| atgcacaggc | ttgcatttga | ggtgtttatg | agacttctta | ttggtgatga | ggttaatcaa |  600 |
| gaatttttg | atcaaatgtt | tgtggagatt | actgctgtaa | ttagtgctgt | tcacaacttg |  660 |
| ccaattaatc | tcccaggatt | tccttatcat | aagggactca | aggctcgaaa | agtactagga |  720 |
| gggatatttc | aaaaactaat | agatgaaaga | gagaagccca | tgaaggatgg | aaaatcaatg |  780 |
| ccaagggcaa | acataattga | tatgttgtta | tcaaacacta | atcaagatta | tgaagacaat |  840 |
| atattgagtg | acagaagat | cgttgaaatc | ctagttttgt | tttcatttgc | tggttttgaa |  900 |
| cctgttgctc | ttatgtctgt | caaggcaatt | tttcacttgc | aaaagcatcc | ccatttcttg |  960 |
| gagaaagcca | agaggaaca | agaggaaata | gtaaagagaa | gagcatcttc | aaatgctgga | 1020 |
| cttagttttg | atgagattag | gcaaatgacg | tttgttagta | aggtaattaa | tgaaacgtta | 1080 |
| cgtattgcta | ctgatcaaac | ggtattcctt | agagacacaa | gtactacttt | taacataaat | 1140 |
| gggtacacca | tacccaaagg | gtggaagttt | tttgcagttg | tatggaatat | tcatatgaat | 1200 |
| cctgatgttt | atgttcagcc | taaggaattt | aatccttcaa | gatgggatga | tattgaaact | 1260 |
| aagccaggca | ttttcttcc | attttcaatg | ggccccaaat | catgcccagg | atccaatctg | 1320 |
| gccaagcttc | aaatttcagt | aattcttcat | tattatcttc | ttcactacag | ggttgagcaa | 1380 |
| attaatccag | aggctagatg | ttatcctcct | gaaaattgtc | ttgtgaaatt | caagaagctc | 1440 |
| tcaatctcta | gtgatggtaa | c | | | | 1461 |

```
<210> SEQ ID NO 3
<211> LENGTH: 487
<212> TYPE: PRT
<213> ORGANISM: Solanum lycopersicum

<400> SEQUENCE: 3

Met Asp Phe Tyr Asn Leu Ala Leu Phe Phe Ile Ala Leu Ile Leu Gly
 1               5                  10                  15

Ile Phe Thr Phe Tyr Ala Ile Leu Met Arg Ile Asn Gly Trp Tyr Tyr
             20                  25                  30

Ala Ile Lys Phe Cys Ser Asn Lys Tyr Asn Ile Pro Asn Gly Tyr Met
         35                  40                  45

Gly Leu Pro Tyr Phe Gly Asn Thr Leu Ser Tyr Phe Lys Ala Ser Met
     50                  55                  60

Cys Gly Asp Pro Lys Ser Phe Ile Asp Phe Phe Ala Thr Arg Phe Gly
 65                  70                  75                  80

Glu Gly Gly Met Tyr Arg Ala Tyr Ile Phe Gly Lys Pro Thr Ile Met
                 85                  90                  95

Val Thr Lys Pro Glu Ile Ile Arg Lys Val Leu Met Asp Glu Glu Tyr
            100                 105                 110

Leu Glu Arg Gly Leu Pro Asn Tyr Met Lys Lys Leu Ile Gly Leu Thr
        115                 120                 125

Thr Ser Ile Glu Glu Asp Lys Tyr Phe Arg Arg Leu Thr Ala Pro Val
130                 135                 140

Lys Ser His Gly Leu Leu Ser Asp Tyr Phe Asp Tyr Ile Asp Lys Thr
145                 150                 155                 160

Val Ser Ser Thr Leu Glu Lys Tyr Ala Thr Thr Glu Glu Pro Val Glu
                165                 170                 175

Phe Leu His Lys Met His Lys Leu Thr Phe Glu Val Phe Met Arg Leu
            180                 185                 190

Leu Ile Gly Asp Glu Val Asn Gln Glu Leu Phe Asp Glu Met Phe Glu
        195                 200                 205

Glu Ile Thr Ala Val Ile Ser Gly Val His Asn Leu Pro Ile Asn Leu
    210                 215                 220

Pro Gly Phe Ala Tyr His Lys Gly Leu Lys Ala Arg Lys Val Leu Gly
225                 230                 235                 240

Glu Val Phe Lys Lys Leu Ile Asp Glu Arg Glu Ala Met Lys Asp
                245                 250                 255

Gly Lys Ser Met Pro Lys Ala Asn Ile Ile Asp Met Leu Leu Ser Asn
            260                 265                 270

Asn Asn Gln Asp Tyr Glu Ala Asn Met Leu Ser Asp Lys Lys Ile Ile
        275                 280                 285

Glu Ile Leu Val Leu Phe Ser Phe Ala Gly Phe Glu Pro Val Ala Leu
    290                 295                 300

Met Ser Val Lys Ala Ile Phe His Leu Gln Lys His Pro His Phe Leu
305                 310                 315                 320

Glu Lys Ala Lys Glu Glu Gln Glu Glu Ile Val Lys Arg Arg Ala Ser
                325                 330                 335

Ser Asn Ala Gly Leu Ser Phe Asp Glu Ile Arg Gln Met Thr Phe Val
            340                 345                 350

Ser Lys Ile Ile Asn Glu Thr Leu Arg Ile Ala Thr Asp Gln Ser Val
        355                 360                 365

Phe Leu Arg Asp Thr Ser Thr Thr Phe Asn Ile Asn Gly Tyr Thr Ile
```

```
            370             375             380
Pro Lys Gly Trp Lys Phe Phe Ala Val Val Trp Asn Ile His Met Asn
385                 390                 395                 400

Pro Asp Val Tyr Val Gln Pro Lys Glu Phe Asn Pro Ser Arg Trp Asp
                405                 410                 415

Asp Ile Glu Thr Lys Pro Gly Ile Phe Leu Pro Phe Ser Met Gly Pro
            420                 425                 430

Lys Ser Cys Pro Gly Ser Asn Leu Ala Lys Leu Gln Ile Ser Val Ile
        435                 440                 445

Leu His Tyr Tyr Leu Leu His Tyr Arg Val Glu Gln Ile Asn Pro Glu
    450                 455                 460

Ala Arg Cys Tyr Pro Pro Glu Asn Cys Leu Val Lys Phe Lys Lys Leu
465                 470                 475                 480

Ser Ile Ser Ser Asn Gly Asn
            485

<210> SEQ ID NO 4
<211> LENGTH: 1461
<212> TYPE: DNA
<213> ORGANISM: Solanum lycopersicum

<400> SEQUENCE: 4
atggatttct acaatttagc cttgttcttc atagctttaa tacttggaat tttcacattt      60
tatgccatat taatgagaat aaatggttgg tattatgcaa tcaaattttg ttcaaacaaa     120
tataacatcc caaatggtta tatgggtttg ccatattttg gtaacacact ttcttacttc     180
aaagcttcaa tgtgtggtga tccaaaatca ttcattgatt tctttgctac taggtttgga     240
gaaggaggaa tgtataggge atacatattt gggaagccaa caattatggt gacaaagcca     300
gaaataatta gaaaagtttt gatggatgaa gagtatcttg aaagaggttt gcctaattat     360
atgaaaaaat taattggatt aacaacttcg atagaagaag acaaatattt tcgtagatta     420
acagcaccag taaaaagtca tggattatta tctgattatt tcgattatat cgataaaact     480
gtgagttcta cattagagaa atacgctact acggaagaac ctgttgagtt tcttcataaa     540
atgcacaagc ttacgtttga ggtgtttatg agactttta ttggtgatga agttaatcaa     600
gaattatttg atgaaatgtt tgaggagatt actgctgtaa ttagtggtgt tcacaatttg     660
ccaattaatc tcccaggatt tgcttatcat aagggactca aggctcgaaa agtactagga     720 gaggtatttta aaaattaat tgatgaaaga agagaagcca tgaaggatgg aaaatcaatg     780
ccaaaggcaa acataattga tatgttgtta tcaaacaaca atcaagatta tgaagcaaac     840
atgttgagtg acaagaagat cattgaaatc ctagttttgt tttcatttgc tggttttgaa     900
cctgttgctc ttatgtctgt caaggcaatt ttccacttac aaaaacatcc acatttcttg     960
gaaaaagcca agaggaaca agaggaaata gtaaagagaa gagcatcttc aaatgctgga    1020
cttagttttg atgaaattag acaaatgaca tttgttagta agataattaa tgaaacgtta    1080
cgtatagcta ctgatcagtc ggtattcctt agagacacaa gtactacttt taacataaat    1140
gggtacacca tacccaaagg gtggaagttt tttgcagttg tatggaatat tcatatgaat    1200
cctgatgttt atgttcaacc taaggaattt aatccttcga gatgggatga tattgaaact    1260
aagccaggca tttttctacc tttttcaatg ggccccaaat catgcccagg atccaatttg    1320
gccaagcttc aaatttcagt aattcttcat tattatcttc ttcactacag ggttgagcaa    1380
attaatccag aggctagatg ttatcctcct gaaaattgtc ttgtgaaatt caagaagcta    1440
```

```
tcgatctcta gtaatggtaa t                                              1461
```

<210> SEQ ID NO 5
<211> LENGTH: 5439
<212> TYPE: DNA
<213> ORGANISM: Solanum tuberosum

<400> SEQUENCE: 5

```
gaggctaaga aaaagagaga gagagaacat ggatttctac aatttagcct tattcttcat      60
agctttagta attgggattt tcacatttta tgctatatta atgagaatta atggttggta     120
ttatgcaatc aaattttgtt caaagaaata taacatccct ctaggttata tgggtttgcc     180
atattttggc aacacacttt cttacttcaa atctaccatt tgtggtgatc caaattcatt     240
ccttgatttc tttgctacta ggtaaattaa ctattttcat tatcgtactt atttgctatg     300
ttgtttgaat tcttgaaaaa tattaatatg tacttgtcaa atcttttaaa aatagtgcat     360
ttttgaagaa tctaacatga gtactgcaac tgttattaca attacatttt tgtagagtcc     420
aattgaacaa aattttttctt tttttttttt aaaggtttgg gacaggagga atgtataggg     480
catacatatt tgggaagcca acaattatgg tgacaaagcc agaaataatt agaaaagttt     540
tgatggatga agaatatctt gaaagaggtt tgcctaatta tatgaaaaaa ttaattggat     600
taacaacttc gattgaagaa gataaatatt ttcgtcgatt aacatctcca gtaaaaagtc     660
atggattatt atccgattat tttgattata tcgataaaac tgtgagcact acattagaga     720
aatacgctac tacggaagaa cctattgagt ttctccataa gatgcacagg cttgcatttg     780
aggtgtttat gagacttctt attggtgatg aggttaatca agaattttt gatcaaatgt     840
ttgtggagat tactgctgta attagtgctg ttcacaactt gccaattaat ctcccaggat     900
ttccttatca tagggactc aaggtaagat gtgttcaaac ttttaatatt atttttattt     960
cattttaaat ttttaataat cataagatat aaatgtgttt tttaacttg ccatcagttt    1020
atatttgtgc ccttcaattt tgagtgtgta taaatttgaa ttagtagaca catgacataa    1080
tatatgtagg acatcatgta ggatgcaaac tgtcacgaag aacgtgtgtg tttacttgtt    1140
caactttata taagtttaag tgtctacttg tgtgtgtcca aaattgaagg gtacacatgt    1200
gagatgaggc caagttaaat ggcatattta tatattttag atagaataac atgtttttt    1260
ttatatacat aatatataaa tctgcccttc gatttggatt caactgacat ctatgccctc    1320
caactttagg tgtgcacaaa catatgctta aacatgtata aaaatgaaca aatagacaca    1380
tttgtcttaa ctggcacaca tgacaatttt gtgtcctacg tgatgcccta catgtattat    1440
gttacgcagg acatgtgtgt caacttgttt aatttatac aagtttaagt gtctatttgt    1500
acacacccaa aattagttga agccaagtta aatgacatat ttatgtatta tatatttct    1560
acatacataa ttacatgtgt gggagcccca accacctctt ttattttttt aataattggt    1620
gatggtggtg attagagaga ctagaattaa agatatttgt tctgttgtaa taccattatt    1680
gaattgtacg gctacttcat ttaaggaact attgatttaa tttaagtgca acactctttt    1740
cacaaatcaa gaactacgaa gggtgtgttt ggtatgaaag gaaaacattt tccagaaaat    1800
gcttttcaat tttctcatgt ttggttgggt aaaatgtttt ggaaatgttt tccaaatcaa    1860
cttatttttcc tcaaatttaa ggaaaatgac ttcccctcaa aaattaagaa aaacattttc    1920
caaaactctc ctacaacttt aaattacaat ttatattttt tgaaaaaatc aattttttt    1980
gttgaaaaaa aaattaaagc tttttttttaa aaaaaaaaa tcgacttcaa ttttttaattt   2040
ttttttatccc accctcaccc cctactccct accccgccaa atccccttcc accccacaaa   2100
```

```
aaaaattaag ttttttttta aaaaatgttt ccaatttaaa ttttattttt tcatcccacc    2160 ccctcccttta ccctcgacct cctcccacc atccccccta cacccaaaaa attcaaaaaa    2220
taaagttggt tctaaaatat atttctaatt caaattctta tttttcatcc acccaccccc    2280
cggccagccc acccccacca aaaaaaatta agtttgtttt taaaaaaata ttttttattt    2340
caaattttta tttttccacc ccaccccta cccgcgaccc cccatcagcc ccccacccc     2400 tccaaaaaaa aatttaagtt tattttaaaa aaaatttt caatttcatt ttttgttttt      2460
tcaccccacc ccctacccgc cagcctcacc ccccaacccc accctcccc aaaaaattt      2520 aagtttattt taaaaaaaat attttcagtt tcaattcaaa aaattattct ctctagttag   2580
aataaaagat attttctcaa aaaaaaaat cattcataaa tcaaacacat aaaaatcttt    2640
ttcgaaaaat attttatact caccaaccaa acatgagaaa ataagtccaa agtctactta   2700
ttttccagga aaacattttc cttcataccg aacacacccg aaatcacccc tttcatcttt   2760
tatcgtgata tttgtggttg taataaacat aatatagagt gcaacatgca tgtcaaagac   2820
caaaaactat gagatcactc ttttcattta atatttatcg tgttgtatat gtttattatg   2880
atttcaggct cgaaaagtac taggagggat atttcaaaaa ctaatagatg aaagaagaga   2940
gaagcctgaa ggatggaaaa tcaatgccaa gggcaaacat aattgatgtg ttgttatcaa   3000
acactaatca agattatgaa gacaatatat tgagtgacaa aagatcgtt gaaatcctag    3060 ttttgttttc atttgctggt tttgaacctg ttgctcttat gtctgtcaag gcaattttc    3120 acttgcaaaa gcatcccccat ttcttggaga aagccaaagt aagtactctt tattctgttt  3180
taggggtgtc atatgggtga gttaaactga atttggacag gtggactgag ttaattagtc   3240
caaaacttac ttggactaaa atggactaac aaacgagtca taaactcaac tcgtctaatt   3300
agacaggttg agttaaattt ggacgaatta aattgggcta agttaatatg tccaaaaatt   3360
tggggctaaa atgagataac aaaaggatca taactcaact cgtctaattg gtcgatccaa   3420
acctaagcgg gttgggtggg tagtgtattc acgagtggat ttgccacccc tagtttattt   3480
tattttatat gacgatattt gattaattat ttttttaaca ggaggaacaa gaggaaatag   3540
taaagagaag agcatcttca aatgctggac ttagttttga tgagattagg caaatgacgt   3600
ttgttagtaa ggtaagacaa tattatgatg ttatatactt tctataatag catttttata   3660
aataatacca ttatacaaaa agtcatcagt acaaataatt aaaaaaagaa gatgaagtga   3720
taatacaaaa attggactaa catgcattat tatttattaa tgttatctct tttaatattg   3780
acaggtaatt aatgaaacgt tacgtattgc tactgatcaa acggtattcc ttagagacac   3840
aagtactact tttaacataa atggttggta ctttgcctta ttcttttgta tttatattat   3900
tattttctat cgaaaaatca aaatacgaca aatattttga aacgacgaat aattcattca   3960
ttcatttatc tcttgtatgt gtagggtaca ccatacccaa agggtggaag ttttttgcag   4020
ttgtatggaa tattcatatg aatcctgatg tttatgttca gcctaaggaa tttaatcctt   4080
caagatggga tgtaagtgat atgcatctta attaattgtg tttaagaaaa aaattcactt   4140
tatttttttt ataatcaaga aattttttgag ggttaataat gtatgattca aaatatgtta   4200
cgtaataagt tgtgtttgcc ttttaccact ttgaatatta ggtattttat ttgcagtagg   4260
gtttaaactc atgacgagaa tttatttata cataagaata ttagtaaaat tagctcataa   4320
aaatatgatt tgttcaatgt cttatttatt aattcaatta attttgactc atctaattta   4380
attcatctaa aaaatagtgc taggataata ataataataa taataaaatc ggaaatgtgc   4440
```

```
tctaaactag aaccacgccc tccactagga agaaaaaaaa ttgattaaca atctcttaac      4500
attcttcaaa cctaattttg aacctcggta tgttctccta ttttgagtta tagcctcgat      4560
gagttaaaga cgaatcatgt catatctagc taatcaattc ttttcaaatc ttcctcgatc      4620
tatctctacc tctccttaaa catcgttgtc aatcttttgt accttaggag taaaagatag      4680
gatattagtt gctttaccgt tctcaatggt acatagctaa aaagtgtatt atcatcagga      4740
caatgcatgt gttcctcctt ttgagatatc tgaactatct caatttaact ttttacgtta      4800
cgaaaatcat tcccacatta cttattactt aatgatcaag tgaaatttga caggatattg      4860
aaactaagcc aggcatttt t cttccatttt caatgggccc caaatcatgc ccaggatcca      4920
atctggccaa gcttcaaatt tcagtaattc ttcattatta tcttcttcac tacaggtaat      4980
taaatagctt catacttata atatgaaaaa attaactaat tatatttga atattttatt       5040 ttattttctt accaaatatt ttcaaaggga ctaaaatata tgaatttatt gtgaaattta      5100
taccaaaaaa taagtatttt gacccttata ctcgtgattt tatcgtatga attgagatgg      5160
atggaatatt taaaataaaa aaggaaatat aaattattga ttaaatcata ttttaattta      5220
attaaacgat atatttaata ttcatgcagg gttgagcaaa ttaatccaga ggctagatgt      5280
tatcctcctg aaaattgtct tgtgaaattc aagaagctct caatctctag tgatggtaac      5340
taattttaat cattgtgcta caaataaata attcatgttg taatcttgaa aacaataagt      5400
gtattgaata attattaaat tggatgtttt tgtagaacg                             5439

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
gaggctaaga aaagagaga gaga                                                24

<210> SEQ ID NO 7
<211> LENGTH: 23
<212> TYPE: DNA
<213> ORGANISM: Artificial Sequence
<220> FEATURE:
<223> OTHER INFORMATION: primer

<400> SEQUENCE: 7
cgttctacaa aaacatccaa ttt                                                23

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
tgataaggaa atcctgggag a                                                  21

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
```
agagaagcca tgaaggatgg                                            20

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
gaaatacgct actacggaag aacc                                       24

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
cgtcatttgc ctaatctcat c                                          21

<210> SEQ ID NO 12
<211> LENGTH: 29
<212> TYPE: DNA
<213> ORGANISM: Artificial Sequence
<220> FEATURE:
<223> OTHER INFORMATION: primer

<400> SEQUENCE: 12
gagctctaga ggtttgggac aggaggaat                                  29

<210> SEQ ID NO 13
<211> LENGTH: 29
<212> TYPE: DNA
<213> ORGANISM: Artificial Sequence
<220> FEATURE:
<223> OTHER INFORMATION: primer

<400> SEQUENCE: 13
ggatccatat gcaagcctgt gcatcttat                                  29

<210> SEQ ID NO 14
<211> LENGTH: 19
<212> TYPE: DNA
<213> ORGANISM: Artificial Sequence
<220> FEATURE:
<223> OTHER INFORMATION: primer

<400> SEQUENCE: 14
taaagcacga ggaagcggt                                             19

<210> SEQ ID NO 15
<211> LENGTH: 19
<212> TYPE: DNA
<213> ORGANISM: Artificial Sequence
<220> FEATURE:
<223> OTHER INFORMATION: primer

<400> SEQUENCE: 15
gcacaacaga caatcggct                                             19

<210> SEQ ID NO 16
<211> LENGTH: 20
<212> TYPE: DNA

```
<213> ORGANISM: Artificial Sequence
<220> FEATURE:
<223> OTHER INFORMATION: primer

<400> SEQUENCE: 16
taagggactc aaggctcgaa                                                 20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
ttcctctttg gctttctcca                                                 20

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
taaagcacga ggaagcggt                                                  19

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
gcacaacaga caatcggct                                                  19

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
ttaacaggag gaacaagagg                                                 20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
aatgcctggc ttagtttcaa                                                 20

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
catcccatct tgaaggatta aa                                              22
```

<210> SEQ ID NO 23
<211> LENGTH: 56
<212> TYPE: DNA
<213> ORGANISM: Solanum marinasense

<400> SEQUENCE: 23
tggctatttt taataaatta ttccactcct tcttattta tgtgtcataa aattca        56

<210> SEQ ID NO 24
<211> LENGTH: 54
<212> TYPE: DNA
<213> ORGANISM: Solanum marinasense

<400> SEQUENCE: 24
gcgaacatga caattaaaag tggacagaga aaattagata ataatatca ttat          54

<210> SEQ ID NO 25
<211> LENGTH: 66
<212> TYPE: DNA
<213> ORGANISM: Solanum lignicaule

<400> SEQUENCE: 25
cccattaaag tggctatttt taataaatta ttccactcct ttttatttta tgtggcataa   60
aattaa                                                              66

<210> SEQ ID NO 26
<211> LENGTH: 53
<212> TYPE: DNA
<213> ORGANISM: Solanum lignicaule

<400> SEQUENCE: 26
tacaacatga caattaaaag tggacagagg aaatctgata ataatatca tta           53

<210> SEQ ID NO 27
<211> LENGTH: 447
<212> TYPE: DNA
<213> ORGANISM: Solanum marinasense

<400> SEQUENCE: 27
gatgagatta ggcaaatgac gtttgttagt aaggtaagac aatattatga tgttatatac   60
tttctataat agcattttta taataatac cattatacaa aaagtcgtca tcagtacaaa   120
taattaaaaa aagaagatga agtgataata caaaaattgg actaacatgc attattattt   180
attaatgtta tctcttttaa tattgacagg taattaatga aacgttacgt attgctactg   240
atcaaacggt attccttaga gacacaagta ctactttaa cataaatggt tggtactttg   300
ccttattctt ttgtatttat attattattt tctatcgaaa aatcaaaata cgacaaatat   360
tttgaaacga cgaataattc attcattcat ttatctcttg tatgtgtagg gtacaccata   420 cccaagggt ggaagttttt tgcagtt                                       447

<210> SEQ ID NO 28
<211> LENGTH: 110
<212> TYPE: DNA
<213> ORGANISM: Solanum marinasense

<400> SEQUENCE: 28
gatgagatta gacaaatgac ctacgttagt aaggcaagac aatattatga tgtttggcta   60
tttttaataa attattccac tccttcttat tttatgtgtc ataaaattca              110

```
<210> SEQ ID NO 29
<211> LENGTH: 357
<212> TYPE: DNA
<213> ORGANISM: Solanum marinasense

<400> SEQUENCE: 29
gcgaacatga caattaaaag tggacagaga aaattagata aataatatca ttataaaaat      60
tggactaaca tgcattatta tttattcatg tatctctttt aaatattgac aggtaattaa     120
tgaaacattg cgtattgcaa ctgatcagac tgtattcctt cgagacacaa gtactacttt    180
taacataaat ggttggtact ttgccttatt cttttgtatt tatattatta ttttctatcg    240
aaaaatcaaa atactacaaa tattttgaaa cgacgaaaat tgaataattc attcattcat    300
ttatctcttg tatgtgtagg gtacaccata cccaaagggt ggaagttttt tgcagtt      357

<210> SEQ ID NO 30
<211> LENGTH: 120
<212> TYPE: DNA
<213> ORGANISM: Solanum lignicaule

<400> SEQUENCE: 30
gatgagatta gacaaatgac ctatgttagt aaggtaagat aatatcatga tgttcccatt     60
aaagtggcta tttttaataa attattccac tccttttat tttatgtggc ataaaattaa    120

<210> SEQ ID NO 31
<211> LENGTH: 328
<212> TYPE: DNA
<213> ORGANISM: Solanum lignicaule

<400> SEQUENCE: 31
tacaacatga caattaaaag tggacagagg aaatctgata aataatatca ttataaaaat     60
tggactaaca tgcattatta tttatttcat gcatctcttt taatgttgac aggtaattaa    120
tgaaacattg cgtattgcta ctgatcagac tgtattcctt cgagacacaa gtacaacttt    180
taacataaat ggttggtgct ttgccttatt tttttatcga aaaataaaa tgacaaatat    240 tttgagacga ggaaaatcga atgattcatt cacttatctt gtatgtgtag ggtacaccat    300
acccaaaggg tggaagtttt ttgcagtt                                      328
```

PLANT HAVING SUPPRESSED EXPRESSION OF GLYCOALKALOID BIOSYNTHETIC ENZYME GENE OR ALTERED ACTIVITY OF THE ENZYME

CROSS REFERENCE TO RELATED APPLICATIONS

This application is a National Stage of International Application No. PCT/JP2013/056163 filed Mar. 6, 2013, claiming priority based on Japanese Patent Application No. 2012-051011 filed Mar. 7, 2012, the contents of all of which are incorporated herein by reference in their entirety.

TECHNICAL FIELD

The present invention relates to a solanaceous plant such as potato, in which the expression of a glycoalkaloid biosynthetic enzyme gene for producing a glycoalkaloid compound characteristic in a solanaceous plant such as potato is suppressed or the activity of the glycoalkaloid biosynthetic enzyme is altered so as to produce no glycoalkaloids.

BACKGROUND ART

Glycoalkaloids are a group of compounds derived from plants and also referred to as steroidal alkaloids. The structure of glycoalkaloids contains an isoprenoid having a chain with 27 carbon atoms and a nitrogen atom, and it has been reported that 422 species of *Solanum* plants contain glycoalkaloids (Chapter 7.8 of Non-patent Literature 1). As to a plant other than those belonging to the genus *Solanum* in the family Solanaceae, some plants belonging to the family Liliaceae are also known to contain glycoalkaloids. Among glycoalkaloids, important ones are chaconine and solanine from potatoes (*Solanum tuberosum*), and tomatine from tomatoes (*Solanum lycopersicum*), which belong to the genus *Solanum* in the family Solanaceae.

Potato is the fourth most produced crop in the world following corn, rice, and wheat. However, it is a well-known fact that toxic chaconine and solanine are contained in the buds coming out of the tubers or the aerial parts of the plants. Symptoms of poisoning such as abdominal pain, dizziness, and mild disturbance of consciousness are caused by chaconine or solanine. Chaconine and solanine are easily accumulated in tubers when the tubers are damaged or exposed to solar light, and thus there is a risk of poisoning accident caused by improper management of tubers.

These poisoning accidents frequently happen, and recently, a glycoalkaloid poisoning accident occurred at an elementary school in Nara City, Japan on Jul. 16, 2009 (reported by Asahi.com). Potatoes are usually safe foods because they are managed such that the content of glycoalkaloid is maintained at 20 mg/100 g or less by storing potato tubers in a dark place etc. However, in consideration of the risk of such a poisoning accident described above, reducing glycoalkaloids in potato is a matter of concern to all of the persons who deal with potatoes such as the breeding, production, storage, transportation, sale, and purchase of potatoes, but has not been achieved to date. The reasons are as follows. A wild potato species with no glycoalkaloids has not been found, the biosynthetic pathway of glycoalkaloids has remained unconfirmed (FIGS. 7.24A and 7.24B of Non-patent Literature 1, and Non-patent Literature 2), and the identification of genes involved in the biosynthetic pathway has not been proceeded.

Glycoalkaloids exhibit toxicity such as cholinesterase inhibitory activity or membrane disruption effect, but in addition to this, it is known that glycoalkaloids exhibit medicinal effects such as anti-cancer activity, a liver protective effect, an antispasmodic effect, an immune system promoting effect, an antifungal effect, an antiprotozoal effect, and shellfish killing agent activity (Non-patent Literature 1). It has also been reported that esculeoside A, which is a metabolite of glycoalkaloids in tomato, exhibits various physiological effects (Non-patent Literature 3). However, research and development on suppressing the metabolites or efficient production thereof have hardly proceeded since the biosynthetic pathway thereof is not known.

Several enzyme genes catalyzing the transglycosylation process following the aglycone biosynthesis process have been reported (Non-patent Literature 4 to Non-patent Literature 6). However, in Non-patent Literature 4, the gene of UDP-galactosyltransferase, which mediates the conversion of solanidine, which is aglycone, to $\gamma$ solanine, and a strain in which the gene is suppressed have been reported, but the production of chaconine has not been suppressed at all (FIG. 2 of Non-patent Literature 4). In Non-patent Literature 4, the gene of UDP-glucosyltransferase, which mediates the conversion of solanidine to $\gamma$ chaconine, and a strain in which the gene is suppressed have been reported, but the production of both chaconine and solanine is hardly suppressed (FIG. 5 of Non-patent Literature 5). In Non-patent Literature 6, the gene of rhamnosyl transferase, which mediates the conversion of $\beta$ chaconine to $\alpha$ chaconine and $\beta$ solanine to $\alpha$ solanine, has been reported, but the $\beta$-form and $\gamma$-form are increased by the suppression of the gene, although the $\alpha$-form is decreased. As seen from these, by the suppression of the transglycosylation process, the molecular species of glycoalkaloids can be changed but it is very difficult to control the total amount of glycoalkaloids. Recently, an enzyme gene, which catalyzes the oxidative pathway involved in the biosynthetic pathway of glycoalkaloids, has been reported (Patent Literature 1). However, the specific enzyme reaction has remained unclear.

There is a report of an attempt to decrease glycoalkaloids by overexpressing biosynthetic genes of plant sterols or plant hormones (Non-patent Literature 7). However, the amount of glycoalkaloids can only be reduced to about a half at most, and thus an effective means has not been provided in modifying the pathway (FIG. 5 of Non-patent Literature 7).

CITATION LIST

Patent Literature

Patent Literature 1: WO 2011/025011

Non-Patent Literature

Non-patent Literature 1: Eich, Solanaceae and Convolvulaceae: Secondary Metabolite (2008), Springer
Non-patent Literature 2: Ginzberg et al., Potato Research (2009) 52: 1-15
Non-patent Literature 3: Nohara et al., J. Nat. Prod. (2010) 73: 1734-1741
Non-patent Literature 4: McCue et al., Plant Sci. (2005) 168: 267-273
Non-patent Literature 5: McCue et al., Phytochemistry (2006) 67: 1590-1597
Non-patent Literature 6: McCue et al., Phytochemistry (2007) 68: 327-334

Non-patent Literature 7: Arnqvist et al., Plant Physiol. (2003) 131: 1792-1799

Non-patent Literature 8: Heftmann, Phytochemistry (1983) 22: 1843-1860

Non-patent Literature 9: Eckart Eich, 'Solanaceae and Con-Volvulaceae: Secondary Metabolite,' 2008, Springer, Heidelberg, Germany, p. 368-373

Non-patent Literature 10: Kaneko et al., Phytochemistry (1977) 16: 791-793

SUMMARY OF THE INVENTION

Technical Problem

An object of the present invention is to provide a solanaceous plant such as potato, in which the expression of a glycoalkaloid biosynthetic enzyme gene for producing a glycoalkaloid compound is suppressed or the activity of the glycoalkaloid biosynthetic enzyme is altered so as to produce no glycoalkaloids.

Solution to Problem

The inventor has conducted intensive investigations in order to obtain a solanaceous plant such as potato containing no glycoalkaloids. The inventor has revealed a gene encoding a new enzyme involved in biosynthesis of glycoalkaloids in potato plants and the genomic structure thereof. On the basis of the gene and the genomic structure thereof, DNA and RNA were extracted from various potatoes and they were compared with those of potatoes having no mutation in terms of the gene, the genomic structure thereof, and the expression of the gene. As a result, plants having a mutation in the gene encoding the above enzyme and exhibiting suppressed expression of the gene were selected. The inventor has further discovered that a plant variety not producing glycoalkaloids anymore and thus accumulating no glycoalkaloids within the plant can be obtained by crossing with the plant as a mother plant, and thus have completed the present invention. The inventor has discovered that a tomato having a reduced glycoalkaloid content can be produced in the same manner as well.

In other words, the present invention includes the following inventions.

[1] A method of producing a cultivar having a reduced risk of accumulating glycoalkaloids by screening progeny obtained by crossing a plant as a mother plant, in which the expression of an oxidase gene involved in glycoalkaloid biosynthesis is suppressed or the activity of the enzyme is lowered.

[2] The method according to [1], wherein the oxidase gene involved in glycoalkaloid biosynthesis is encoded by a DNA sequence hybridizing to the DNA sequence set forth in SEQ ID NO: 2, 4, or 5 or a complementary sequence to the DNA sequence under a stringent condition.

[3] The method according to [1] or [2], wherein the mother plant is a plant obtained by artificially modifying an oxidase gene involved in glycoalkaloid biosynthesis by mutation treatment, or progeny thereof.

[4] The method according to [1] or [2], wherein the mother plant is a plant obtained by screening a wild-type strain, or progeny thereof.

[5] The method according to [4], wherein the mother plant is a plant containing an insertion sequence in an intron of an oxidase gene.

[6] The method according to [5], wherein the mother plant is a plant containing an insertion sequence that comprises the sequences set forth in SEQ ID NO: 23 and SEQ ID NO: 24 in the $4^{th}$ intron of the oxidase gene, an insertion sequence that comprises the sequence set forth in SEQ ID NO: 25 and the sequence set forth in SEQ ID NO: 26, or an insertion sequence consisting of a partial sequence thereof.

[7] The method according to any one of [1] to [6], comprising detecting a mutation of the oxidase gene involved in glycoalkaloid biosynthesis by a genetic marker upon screening the progeny obtained by the crossing.

[8] The method according to [7], wherein the genetic marker corresponds to a sequence comprising the sequence set forth in SEQ ID NO: 23 and the sequence set forth in SEQ ID NO: 24, or a sequence comprising the sequence set forth in SEQ ID NO: 25 and the sequence set forth in SEQ ID NO: 26, or a partial sequence thereof.

[9] The method according to [7], comprising determining the presence of the genetic marker in the $4^{th}$ intron of the oxidase gene using a sequence comprising the sequence set forth in SEQ ID NO: 23 and the sequence set forth in SEQ ID NO: 24, a sequence comprising the sequence set forth in SEQ ID NO: 25 and the sequence set forth in SEQ ID NO: 26, a partial sequence thereof, or a primer sequence comprising a surrounding sequence.

[10] The method according to any one of [1] to [9], wherein the plant is a solanaceous plant.

[11] The method according to [10], wherein the solanaceous plant is potato.

[12] A cultivar produced by the method of any one of [1] to [11].

The present invention further includes the following inventions.

[13] A protein of the following (a) or (b):
(a) a protein consisting of the amino acid sequence set forth in SEQ ID NO: 1; and
(b) a protein consisting of an amino acid sequence wherein one or several amino acids in the amino acid sequence set forth in SEQ ID NO: 1 are deleted, substituted, inserted, or added, and having glycoalkaloid biosynthetic enzyme activity.

[14] A gene consisting of any DNA of the following (c) to (f):
(c) a DNA consisting of the nucleotide sequence set forth in SEQ ID NO: 2;
(d) a DNA hybridizing to a DNA consisting of a nucleotide sequence complementary to the DNA consisting of the nucleotide sequence set forth in SEQ ID NO: 2 under a stringent condition, and encoding a protein having glycoalkaloid biosynthetic enzyme activity;
(e) a DNA consisting of a nucleotide sequence having a sequence identity of 80% or more with the nucleotide sequence set forth in SEQ ID NO: 2, and encoding a protein having glycoalkaloid biosynthetic enzyme activity; and
(f) a DNA consisting of a degenerate isomer of the nucleotide sequence set forth in SEQ ID NO: 2.

[15] A protein of the following (g) or (h):
(g) a protein consisting of the amino acid sequence set forth in SEQ ID NO: 3; and
(h) a protein consisting of an amino acid sequence wherein one or several amino acids in the amino acid sequence set forth in SEQ ID NO: 3 are deleted, substituted, inserted, or added, and having glycoalkaloid biosynthetic enzyme activity.

[16] A gene consisting of any DNA of the following (i) to (l):
(i) a DNA consisting of the nucleotide sequence set forth in SEQ ID NO: 4;

(j) a DNA hybridizing to a DNA consisting of a nucleotide sequence complementary to the DNA consisting of the nucleotide sequence set forth in SEQ ID NO: 4 under a stringent condition, and encoding a protein having glycoalkaloid biosynthetic enzyme activity;

(k) a DNA consisting of a nucleotide sequence having homology of 80% or more with the nucleotide sequence set forth in SEQ ID NO: 4, and encoding a protein having glycoalkaloid biosynthetic enzyme activity; and (l) a DNA consisting of a degenerate isomer of the nucleotide sequence set forth in SEQ ID NO: 4.

[17] A recombinant vector comprising the gene of [14] or [16].

[18] A transformant into which the recombinant vector of [17] is introduced.

[19] The transformant according to [18], which is a plant.

[20] A method of detecting the presence of a mutation and/or a polymorphism of a gene encoding a glycoalkaloid biosynthetic enzyme in a plant, comprising the steps of:
(i) isolating a nucleic acid that is genomic DNA or RNA from a plant;
(ii) reverse-transcribing the nucleic acid to synthesize cDNA if the nucleic acid of (i) is RNA,
(iii) amplifying a gene fragment comprising the nucleotide sequence set forth in SEQ ID NO: 2, SEQ ID NO: 4, or SEQ ID NO: 5 from the DNA obtained in step (i) or (ii); and
(iv) determining the presence of a mutation and/or a polymorphism in the DNA.

[21] The method according to [20], wherein the plant is a solanaceous plant.

[22] A method of detecting a mutation and/or a polymorphism of a gene encoding a glycoalkaloid biosynthetic enzyme by the method of [20] or [21] and selecting a plant having the mutation and/or the polymorphism.

[23] A plant having a mutation and/or a polymorphism in a gene encoding a glycoalkaloid biosynthetic enzyme, which is selected by the method of [22].

[24] The plant according to [23], which is a solanaceous plant.

[25] The method of selecting a plant according to [23] or [24], wherein a plant having altered ability to express a gene encoding a glycoalkaloid biosynthetic enzyme or altered activity of the encoded glycoalkaloid biosynthetic enzyme with respect to an existing variety.

[26] A plant having altered ability to express a gene encoding a glycoalkaloid biosynthetic enzyme with respect to an existing variety or altered activity of a glycoalkaloid biosynthetic enzyme with respect to an existing variety, which is selected by the method of [25].

[27] The plant according to [26], which is a solanaceous plant.

The present specification includes the contents disclosed in the specification and/or drawings of Japanese Patent Application No. 2012-051011, on which a priority of the present application is based.

Advantageous Effects of Invention

According to the method of the present invention, a solanaceous plant such as potato neither producing nor accumulating glycoalkaloids within the plant can be obtained, in which the expression of an oxidase gene involved in glycoalkaloid biosynthesis is suppressed, or, the activity of the enzyme is lowered.

BRIEF DESCRIPTION OF DRAWINGS

FIG. 1-1 illustrates the result of analysis on the homology of a biosynthetic gene E of potato and tomato by DNA analysis software GENETYX (GENETYX CORPORATION). Significantly high homology is seen in general. The top sequence shows nucleotides 1 to 540 of SEQ ID NO: 2 and the bottom sequence shows nucleotides 1 to 540 of SEQ ID NO: 4.

FIG. 1-2 illustrates the result of analysis on the homology of the biosynthetic gene E of potato and tomato by DNA analysis software GENETYX (GENETYX CORPORATION) (continued from FIG. 1-1). The top sequence shows nucleotides 541 to 1200 of SEQ ID NO: 2 and the bottom sequence shows nucleotides 541 to 1200 of SEQ ID NO: 4.

FIG. 1-3 illustrates the result of analysis on the homology of the biosynthetic gene E of potato and tomato by DNA analysis software GENETYX (GENETYX CORPORATION) (continued from FIG. 1-2). The top sequence shows nucleotides 1201 to 1461 of SEQ ID NO: 2 and the bottom sequence shows nucleotides 1201 to 1461 of SEQ ID NO: 4.

FIG. 2 illustrates the structure of a vector for the suppression of gene E. FIG. 2 specifically illustrates the internal structure of the right border (RB) and the left border (LB) of T-DNA of the gene part to be introduced, and the restriction enzyme site.

FIG. 3 shows the glycoalkaloid contents of the in vitro stems of potato transformants.

FIG. 8 illustrates the insertion regions in the 4th intron of gene E of related species of potato (wild species) and the partial nucleotide sequences of the insertion sequences. Sequences of exon portions are indicated with double underlines, conserved 5' splicing sequence is indicated with an underline, and insertion sequences are indicated with thick underlines. As also discussed at paragraph [0079] below, the entire sequence from the 4th exon to the 6th exon of Sassy is set forth in SEQ ID NO: 27. For FTT1, the sequence from the 4th exon to the underlined sequence of SEQ ID NO: 23 is set forth in SEQ ID NO: 28 and the sequence from the underlined sequence of SEQ ID NO: 24 to the 6th exon of FTT1 is set forth in SEQ ID NO: 29. For FTT16, the sequence from the 4th exon to the underlined sequence of SEQ ID NO: 25 is set forth in SEQ ID NO: 30, and the sequence from the underlined sequence of SEQ ID NO: 26 to the 6th exon of FTT16 is set forth in SEQ ID NO: 31.

DESCRIPTION OF EMBODIMENTS

Figure 2:
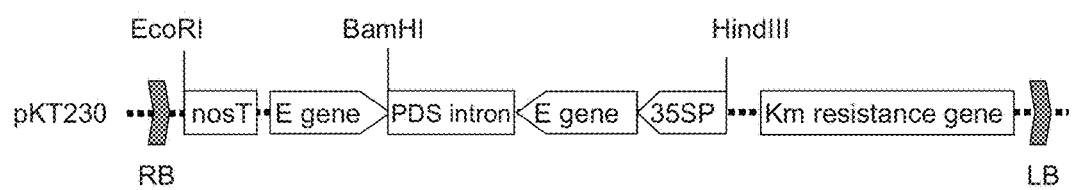

Hereinafter, the present invention will be described in detail.

1. Glycoalkaloid Biosynthetic Enzyme of the Present Invention

The present invention relates to a method of producing a cultivar having a reduced risk of accumulating glycoalkaloids by screening progeny obtained by crossing a plant having the altered activity of oxidase (hereinafter, referred to as a glycoalkaloid biosynthetic enzyme(s)) involved in glycoalkaloid biosynthesis, as a mother plant.

Proteins and enzymes of the present invention, which are involved in glycoalkaloid biosynthesis in plants with the altered activity of glycoalkaloid biosynthetic enzymes, are glycoalkaloid biosynthetic enzymes contained in solanaceous plants (Solanaceae) such as potato. Potato (*Solanum tuberosum*), tomato (*Solanum lycopersicum*), eggplant (*Solanum melongena*), capsicum (*Capsium annum*), and the like are included in Solanaceae such as potato. In addition, the enzymes of the present invention are membrane-bound cytochrome P-450 monooxidases. Glycoalkaloids obtained by the enzymes of the present invention include glycoalkaloids synthesized by solanaceous plants such as potato, and examples thereof include glycoalkaloids of potato such as chaconine and solanine and glycoalkaloids of tomato such as tomatine.

Preferred examples of steroidal compounds to be used as substrates of the glycoalkaloid biosynthetic enzymes of the present invention include cholesterols. Examples of cholesterols include cholesterol, sitosterol, campesterol, stigmasterol, and brassicasterol. The glycoalkaloid biosynthetic enzymes of the present invention are oxidases to oxidize them.

The full-length amino acid sequences of the above wild-type enzymes are set forth in SEQ ID NO: 1 or 3. Moreover, the enzymes of the present invention encompass a protein having an amino acid sequence substantially identical to the amino acid sequence set forth in SEQ ID NO: 1 or the amino acid sequence set forth in SEQ ID NO: 3, and having glycoalkaloid biosynthetic enzyme activity. Here, examples of the substantially identical amino acid sequence include an amino acid sequence in which one or several (1 to 10, preferably 1 to 7, more preferably 1 to 5, still more preferably 1 to 3, and yet more preferably 1 or 2) amino acids are deleted, substituted, inserted and/or added with respect to the amino acid sequence, or an amino acid sequence having a sequence identity of 85% or more, preferably 90% or more, more preferably 95% or more, and particularly preferably 97% or more with the amino acid sequence when calculated using (for example, the default, that is, the initial setting parameter) BLAST or the like (Basic Local Alignment Search Tool at the National Center for Biological Information (US)).

The above genes encoding glycoalkaloid biosynthetic enzymes are referred to as gene E.

The term "sequence identity" as used herein refers to the percentage (%) of the number of identical amino acids or nucleotides in the total number of amino acids or nucleotides including gaps when two amino acid sequences or nucleotide sequences are aligned (a gap(s) or no gap may be introduced, and preferably a gap(s) is introduced), for example.

2. Gene Encoding Glycoalkaloid Biosynthetic Enzyme

The gene (gene E) encoding the above glycoalkaloid biosynthetic enzyme is a gene encoding a glycoalkaloid biosynthetic enzyme having activity of oxidizing a steroidal compound.

Examples of DNA encoding the above enzyme include nucleotide sequences encoding the amino acid sequences set forth in the above SEQ ID NO: 1 and SEQ ID NO: 3, respectively. Specific examples thereof include the nucleotide sequences set forth in SEQ ID NO: 2 and SEQ ID NO: 4.

DNA encoding the above enzyme is: DNA hybridizing under a stringent condition to DNA having a nucleotide sequence complementary to the nucleotide sequence set forth in SEQ ID NO: 2 or SEQ ID NO: 4; or, DNA having an at least 60%, at least 70%, at least 80%, at least 85%, preferably at least 90%, further preferably at least 95%, particularly preferably at least 97%, 98% or 99% sequence identity with the nucleotide sequence set forth in SEQ ID NO: 2 or 4, when calculated using known algorithm such as BLAST or FASTA for homology search (for example, the default; that is, the initial setting parameters are used); or, DNA encoding a protein comprising an amino acid sequence, in which 1 or a plurality of, preferably 1 or several, such as 1 to 10, preferably 1 to 7, further preferably 1 to 5, further preferably 1 to 3, further preferably 1 or 2 amino acids are deleted, substituted, inserted and/or added with respect to the amino acid sequence of the protein to be encoded by such DNA.

These DNAs may be homologs, analogs, or mutants of DNAs comprising the nucleotide sequences set forth in SEQ ID NO: 2 and SEQ ID NO: 4. Such DNA can be obtained from leaves, roots, seeds, and the like of plants generating glycoalkaloids, such as plants of the family Solanaceae (e.g., potato (*Solanum tuberosum*) and tomato (*Solanum lycopersicum*)) through hybridization, PCR amplification, or the like.

The term "stringent condition" as used herein refers to a condition where DNA with a high sequence identity hybridizes. Such a condition can be adequately determined by those skilled in the art. For example, such a condition comprises about 1×SSC, 0.1% SDS, and 37° C. A more stringent (moderately stringent) condition comprises about 0.5×SSC, 0.1% SDS, and 42° C. An even more stringent (highly stringent) condition comprises about 0.1-0.2×SSC, 0.1% SDS, and 65° C. Hybridization may be followed by washing with 0.1×SSC and 0.1% SDS at 55 to 68° C., by which stringency can be increased. Here, 1×SSC buffer comprises 150 mM sodium chloride and 15 mM sodium citrate (pH 7.0).

Hybridization conditions and procedures for PCR are described in F. M. Ausbel et al., Short Protocols in Molecular Biology, 3rd ed., John Wiley &Sons, 1995, for example.

Furthermore, examples of DNA encoding the glycoalkaloid biosynthetic enzyme of the present invention further include DNA comprising a sequence (degenerate sequence) based on the degeneration of genetic codes in the nucleotide sequence set forth in SEQ ID NO: 2 or SEQ ID NO: 4.

3. Recombinant Vector

The DNA of the present invention is inserted into an appropriate vector containing a regulatory sequence, so that it can be expressed. The thus obtained recombinant DNA is a recombinant vector.

Vectors to be used herein include all vectors that can be used in procaryotic cells or eukaryotic cells. Examples thereof that can be used herein include vectors for microorganisms such as bacteria (e.g., the genus *Escherichia*, the genus *Pseudomonas*, the genus *Bacillus*, and the genus *Rhodococcus*), filamentous bacteria (the genus *Aspergillus*, the genus *Neurospora*, the genus *Fusarium*, the genus *Trichoderma*, and the genus *Penicillium*), basidiomycetes (e.g., *Phanerochaete chrysosporium*), yeast (e.g., the genus *Saccharomyces*, the genus *Pichia*, and the genus *Candida*), vectors for plant cells and vectors for insect cells.

Examples of a vector for bacteria include vectors of pBR, pUC, pET, and pBluescript series. Examples of a vector for yeast include, but are not limited to, pDR196, pYES-DEST 52, YIp5, YRp17, and YEp24. Examples of a vector for plant cells include, but are not limited to, pGWB, pBiE12-GUS, pIG121-Hm, pBI121, pBiHyg-HSE, pB119, pBI101, pGV3850, and pABH-Hm1 vectors. Examples of a vector for insect cells include, but are not limited to, pBM030, pBM034, and pBK283 vectors.

Components related to the expression, regulation, or secretion of a gene such as a promoter, a terminator, an enhancer, Shine-Dalgarno sequence, a ribosome binding sequence, and a signal sequence are incorporated into vectors to be used in the present invention, and a selection marker (for example, a drug resistant gene and a reporter gene) is included therein if necessary.

Examples of a promoter include, but are not limited to, a lac promoter, a trp promoter, a recA promoter, a tac promoter, a λPL promoter, a T7 promoter, a CaMV35S promoter, an ADH1 promoter, a GAL promoter, a PHO5 promoter, a PGK promoter, and a GAPDH promoter.

Examples of a drug resistant gene include a kanamycin resistant gene, an ampicillin resistant gene, and a hygromycin resistant gene. Examples of a reporter gene include a lacZ gene, a GFP gene, a GUS gene, and a luciferase gene. Examples of other selection markers include an NPTII gene, and a dihydrofolate reductase gene.

The components related to the expression, regulation, or secretion of a gene are preferably incorporated into recombinant vectors depending on the property thereof and in a manner allowing each component to function. Such an operation can be appropriately carried out by those skilled in the art.

4. Transformant

The transformant of the present invention is a transformant retaining the recombinant vector of the present invention. The transformant can be obtained by introducing the recombinant vector, in which a gene encoding an enzyme is inserted, into a host so that the target gene can be expressed. As the host, a host suitable for the vector may be used. Examples thereof include yeast, plant cells, insect cells (Sf9 or the like), and plant viruses. Preferable examples include yeast, plant cells, and plant viruses. The introduction method of the recombinant vector is not particularly limited, as long as it is a method for introducing DNA into a microorganism. Examples thereof include methods using calcium ion [Cohen et al., Proc. Natl. Acad. Sci., U.S.A., 69: 2110 (1972)], electroporation methods, and tri-parental crossing methods. In addition, examples of a method of preparing a transgenic plant include methods using a Ti plasmid or a Ri plasmid of a virus or *Agrobacterium* as a vector. Examples of the host plant include monocotyledons such as rice, wheat, and corn, and dicotyledons such as soybean, rapeseed, tomato, and potato. The transgenic plant can be obtained by regenerating a plant cell transformed with a gene of the present invention. The regeneration of a plant from a plant cell can be carried out by a known method.

5. Production of Glycoalkaloid Biosynthetic Enzyme and Production Method of Glycoalkaloid Compound The glycoalkaloid biosynthetic enzymes of the present invention are membrane-bound cytochrome P-450 monooxidases, and can be collected from general plant bodies [e.g., Collu et al., 2001, FEBS Lett. 508:215-220]. Further, for example, they can be produced by mass production using a microorganism, such as yeast, or an insect cell expression system which is transformed with a gene of the present invention. Examples of insect cells include those disclosed by Morikawa et al., [2006, Plant Cell 18:1008-1022].

Since a protein having high activity can be expressed using these systems, a glycoalkaloid compound can be produced by adding a substrate of the glycoalkaloid biosynthetic enzyme to a culture solution of transformed yeast or insect cells. For example, it is possible to produce efficiently a large amount of an oxidized cholesterol by administering cholesterol as a substrate to the culture solution of transformed yeast. It has been reported (Harada and Misawa 2009 Aug. 12. Epub Appl Microbiol Biotechnol.) that yeast has a pathway (mevalonate pathway) to biosynthesize DMAPP in the cytosol, and a precursor or a substrate can be produced by introducing the mevalonate pathway into *Escherichia coli*. The use of this method enables simultaneous expression of another gene and a membrane-bound cytochrome P-450 monooxidase and production of a glycoalkaloid. Chang et al., [2007 Nat. Chem. Biol. 3:274-277] have reported an example of obtaining a metabolite by expressing such membrane-bound cytochrome P-450 monooxidase in *Escherichia coli*. Seki et al., have reported an example obtaining the same in yeast [2008 PNAS 105:14204-14209]. It becomes possible to produce a glycoalkaloid compound by combining such methods.

6. Gene Suppression Method

The present invention provides a method of suppressing a glycoalkaloid biosynthetic enzyme gene in a plant. As the suppression method, it is possible to use a method of suppressing the expression of the gene such as an RNAi method involving genetic recombination, an antisense method, a PTGS method using a viral vector, or a method of directly introducing a small RNA or the like. In addition, the suppression method may be a method of modifying the genome itself such as a ZFN (zinc finger nuclease) method, a TALEN (Tale nuclease) method [Science, 333, 307 (2011)], or a Cre-lox P site-specific recombination method. A method utilizing the sequence provided by the present invention as an introduction site for a direct mutation is included in these methods. Alternatively, it is also possible to delete the entire region of a glycoalkaloid gene by specifying the sequence of the proximity region from the sequence provided by the present invention, the genome information, and the like and utilizing the sequence of the proximity region.

7. Selection of Genetic Mutation, Polymorphic Individual, Gene Expression Variation The present invention provides a method of detecting the presence of a glycoalkaloid biosynthetic enzyme gene mutation in a plant, a polymorphism such as a single nucleotide polymorphism (SNP), and a gene expression variation. The mutant individual may be produced by radiation, chemical treatment, UV irradiation, or spontaneous mutation.

This method includes a step of isolating genomic DNA or RNA from mutant plant individuals, various plant varieties, and, in the latter case, a step of reverse-transcription to synthesize cDNA, a step of amplifying the gene fragment containing the glycoalkaloid biosynthetic enzyme gene from the DNA using a DNA amplification technique, and a step of determining the presence of a mutation in this DNA. A commercially available kit (for example, DNeasy or RNeasy (QIAGEN)) can be used in a method for extracting DNA or RNA. A commercially available kit (for example, SuperScript First-Strand System (Invitrogen)) can also be used in a method for the synthesis of cDNA. As the method of amplifying a gene fragment with the use of a DNA amplification technique, a technique such as a so-called PCR method or a LAMP method can be used. These mean a group of techniques based on the use of the polymerase to achieve the amplification (that is, increasing the copy number) of a specific DNA sequence by a continuous polymerase reaction. This reaction may be used in place of cloning, and the information on the nucleic acid sequence is only needed. Primers complementary to the sequence of DNA to be amplified are designed to perform DNA amplification. Next, the primers are generated by automated DNA synthesis. The DNA amplification method is well known in the art, and can be easily performed by those skilled in the art on the basis of the teachings and instructions provided in the present specification. Several PCR methods (and related techniques) are disclosed in, for example, U.S. Pat. Nos. 4,683,195, 4,683,202, 4,800,159, 4,965,188, and PCR Protocols: A guide to method and applications edited by Innis et al.

In the step of determining the presence of a mutation or a polymorphism in DNA, a detection method utilizing the homology of a mutant gene and the normal gene, such as a TILLING method (Till et al., 2003, Genome Res 13: 524-530) to detect a mutant using the determination of the nucleotide sequence (Applied Biosystems) or an enzyme that cleaves one side of a mismatched pair may be used. These can be performed by comparing the sequence data obtained from the technique with the gene part of the nucleotide sequence set forth in SEQ ID NO: 2, 4, or 5.

In the step of determining a difference in the mRNA amount, a quantitative PCR such as an RT-PCR method and a real-time PCR method may be adopted for the cDNA using primers prepared based on the nucleotide sequence set forth in SEQ ID NO: 2 or SEQ ID NO: 4. Thereafter, the difference in the mRNA amount can be determined, for example, by comparing with the amount of cDNA obtained from the variety "Sassy".

In a particularly preferred embodiment, the method of determining the presence of a mutation in a glycoalkaloid biosynthetic enzyme gene, which is defined above, is applied to the material obtained from potato (*Solanum tuberosum*) or a related species thereof among solanaceous plants (Solanaceae) (Example 7).

Among the wild species belonging to the potato or related species thereof, there are a large number of wild species whose genotypes and phenotypes related to glycoalkaloid biosynthesis are unknown. By screening these wild species, it is possible to select a wild-type strain which has a mutation in a biosynthetic gene and in which the accumulation of glycoalkaloid is not detected or is reduced compared with cultivated species, or a strain that can cause a decrease in the accumulation of glycoalkaloids by crossing (Example 8).

By the above described method of determining a mutation and/or a polymorphism, it is possible to identify, at the nucleotide level, a mutation or a polymorphism in a gene encoding a glycoalkaloid biosynthetic enzyme, further, it is possible to select a plant having a mutation and/or a polymorphism in a gene encoding a glycoalkaloid biosynthetic enzyme. The present invention includes a plant having a mutation or a polymorphism in a gene encoding a glycoalkaloid biosynthetic enzyme obtained in this manner.

In addition, it is possible to determine a mutation or a polymorphism, determine a difference in the amount of mRNA, and select a plant having altered ability to express a gene encoding a glycoalkaloid biosynthetic enzyme or altered activity of a glycoalkaloid biosynthetic enzyme.

Here, the altered ability to express a gene encoding a glycoalkaloid biosynthetic enzyme or altered activity of a glycoalkaloid biosynthetic enzyme includes an alteration caused by an artificial mutation, a spontaneous mutation conserved in wild species or the like, or a genetic polymorphism. The term "altered activity" refers to a decrease or an increase in activity. The modification of the activity of a glycoalkaloid biosynthetic enzyme includes the decrease or elimination of the inherent normal function of the glycoalkaloid biosynthetic enzyme.

Figure 8:
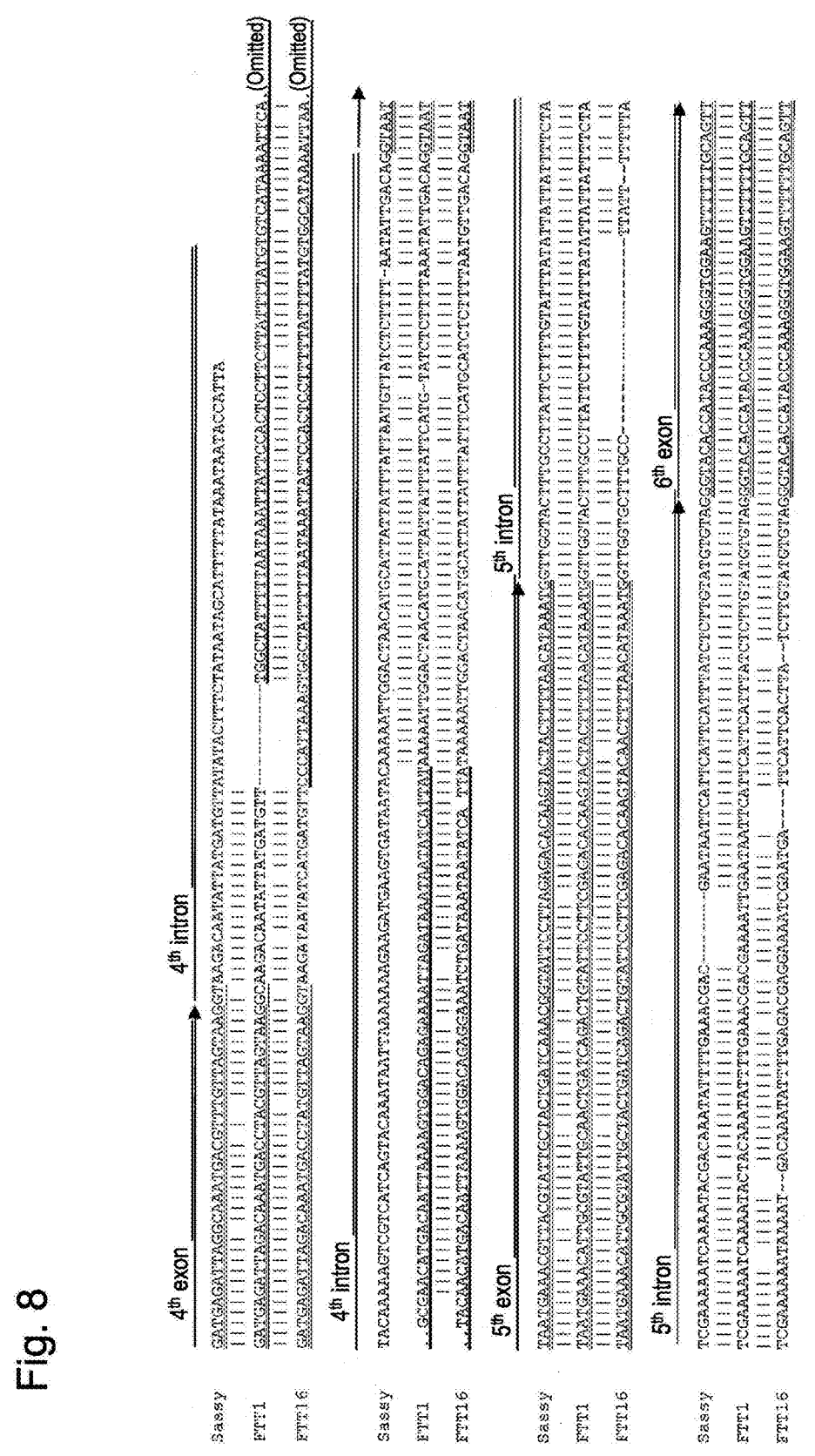

Examples of such a mutation in a gene include the deletion of the entire gene or a partial gene in a glycoalkaloid biosynthetic gene, the substitution of some nucleotides with other nucleotides, and the insertion of a nucleotide(s). Examples of the insertion of a nucleotide(s) include the insertion of tens to hundreds of contiguous nucleotides in an exon of a glycoalkaloid biosynthetic gene. Examples of the substitution of some nucleotides with other nucleotides include the substitution of conserved 5' splicing sequence in an intron and the insertion of a sequence in an intron, by which substitution a normal splicing does not occur. Specific examples thereof include, in a glycoalkaloid biosynthetic gene, the insertion of a sequence comprising the sequence set forth in SEQ ID NO: 23 and the sequence set forth in SEQ ID NO: 24, and the insertion of a sequence comprising the sequence set forth in SEQ ID NO: 25 and the sequence set forth in SEQ ID NO: 26. In such a sequence comprising the sequence set forth in SEQ ID NO: 23 and the sequence set forth in SEQ ID NO: 24, the sequence set forth in SEQ ID NO: 23 is the 5'-terminal sequence, and the sequence set forth in SEQ ID NO: 24 is the 3'-terminal sequence. Also, in the sequence comprising the sequence shown in FIG. 25 and the sequence set forth in SEQ ID NO: 26, the sequence set forth in SEQ ID NO: 25 is the 5'-terminal sequence, and the sequence set forth in SEQ ID NO: 26 is the 3'-terminal sequence. In FIG. 8, the positions of sequences inserted into introns are shown. Sequences indicated with thick underlines are insertion sequences into introns. In FTT1, a sequence containing the 5' terminal sequence set forth in SEQ ID NO: 23 and the 3' terminal sequence set forth in SEQ ID NO: 24 is inserted. The information of the sequence between SEQ ID NO: 23 and SEQ ID NO: 24 is not shown. Moreover, in FTT16, a sequence containing the 5'-terminal sequence set forth in SEQ ID NO: 25 and the 3'-terminal sequence set forth in SEQ ID NO: 26 is inserted. The information of the sequence between SEQ ID NO: 25 and SEQ ID NO: 26 is not shown. This sequence was inserted, in an intron; that is the $4^{th}$ intron between the $4^{th}$ exon and the $5^{th}$ exon, and thus is present. The present invention also includes a plant having such a genetic mutation. The present invention also includes the selection of a plant having such a genetic mutation and the use thereof as a mother plant. Moreover, it is possible to produce a cultivar with a reduced risk of accumulating glycoalkaloids by screening the progeny obtained by crossing the plant as a mother plant.

In addition, in the sequences shown in FIG. 8, the entire sequence from the $4^{th}$ exon to the $6^{th}$ exon of Sassy is set forth in SEQ ID NO: 27, the sequence from the $4^{th}$ exon to the sequence set forth in SEQ ID NO: 23 of FTT1 is set forth in SEQ ID NO: 28, the sequence from the sequence set forth in SEQ ID NO: 24 to the $6^{th}$ exon of FTT1 is set forth in SEQ ID NO: 29, the sequence from the $4^{th}$ exon to the sequence set forth in SEQ ID NO: 25 of FTT16 is set forth in SEQ ID NO: 30, and the sequence from the sequence set forth in SEQ ID NO: 26 to the $6^{th}$ exon of FTT1 is set forth in SEQ ID NO: 31.

Furthermore, a plant having altered activity of a glycoalkaloid biosynthetic enzyme can also be obtained by modifying the gene encoding the glycoalkaloid biosynthetic enzyme by artificial mutation treatment. The modification by the mutation of glycoalkaloid biosynthetic enzyme activity of a certain plant means the modification from existing varieties of the species of the plant. The existing varieties include a wild type but not wild species that have occurred naturally, unless the wild species have already been industrially used. The existing varieties mean all varieties that exist when a plant having modified glycoalkaloid biosynthetic enzyme activity is obtained, and includes varieties produced by artificial manipulations such as crossing and genetic manipulation. In addition, in the modification of activity, the activity is not necessarily altered with respect to all existing varieties, and if the activity is modified with respect to a specific existing variety, the plant having modified activity is included in the "plants having modified activity of a glycoalkaloid biosynthetic enzyme". The "plants having modified activity of a glycoalkaloid biosynthetic enzyme" also include plants having modified activity without any artificial manipulation but with a mutation in a natural state. It is possible to select a plant having altered activity in a natural state and establish the plant as a novel variety by the method of the present invention. In addition, when a plant having modified activity of a glycoalkaloid biosynthetic enzyme is produced by subjecting an existing variety to mutagenesis treatment, an object to be compared may be the same existing variety or another existing variety other than the variety subjected to the mutagenesis treatment. In addition, crossing a plant that is selected from the nature or produced by mutagenesis treatment and has a mutation or a polymorphism in a gene encoding a glycoalkaloid biosynthetic enzyme may provide a novel plant variety having a fixed mutation in the gene encoding the glycoalkaloid biosynthetic enzyme, and having modified ability to express the glycoalkaloid biosynthetic enzyme gene or modified activity of the glycoalkaloid biosynthetic enzyme.

For example, if the plant is potato (Solanum tuberosum), examples of the existing variety include "Cynthia", "Sassy" (sold by Japan Agribio Company), "Sherry", "Danshaku (Baron)", "May Queen", and "Sayaka (Norin registration number: Norin No. 36)". Here, plants having altered ability to express a gene encoding a glycoalkaloid biosynthetic enzyme or altered activity of the glycoalkaloid biosynthetic enzyme compared with an existing variety include plants having increased or decreased ability to express a gene encoding a glycoalkaloid biosynthetic enzyme, compared with an existing variety and further include plants having increased or decreased activity of a glycoalkaloid biosynthetic enzyme compared with an existing variety. The present invention includes such a plant having altered ability to express a gene encoding a glycoalkaloid biosynthetic enzyme or altered activity of a glycoalkaloid biosynthetic enzyme compared with an existing variety, as well.

Particularly, plants having decreased activity of a toxic glycoalkaloid biosynthetic enzyme are preferable. Such a plant synthesizes a low amount of or cannot synthesize at all the glycoalkaloid biosynthetic enzyme, and has a low content of the glycoalkaloid biosynthetic enzyme or lacks the glycoalkaloid synthetic enzyme, or has low or no activity of the glycoalkaloid synthetic enzyme. As a result, the plant has a low glycoalkaloid content or lacks glycoalkaloids. For example, in the case of potato, glycoalkaloids such as chaconine and solanine are not synthesized, and thus amounts of glycoalkaloids, such as chaconine and solanine, synthesized or present in potato tubers are low. In addition, in the case of tomato, glycoalkaloids such as tomatine are not synthesized, and thus amounts of glycoalkaloids, such as tomatine, synthesized or present in tomato fruits are low.

In the case of potato, in a plant having low activity of the glycoalkaloid synthetic enzyme or lacking the activity, glycoalkaloids such as chaconine and solanine are not synthesized in tubers, or the amount of glycoalkaloids such as chaconine and solanine synthesized in tubers is lower than that of the existing varieties above, and thus the amount of glycoalkaloids such as chaconine and solanine present in tubers is also low.

A cultivar having decreased or eliminated glycoalkaloid accumulation, and having excellent taste or cultivation characteristics can be produced using a plant having a mutation in a glycoalkaloid biosynthetic gene (a mutant strain obtained by artificially modifying an oxidase gene involved in glycoalkaloid biosynthesis via mutagenesis treatment, or a wild-type strain selected by screening) as a mother plant. In the present invention, a cultivar having decreased or eliminated glycoalkaloid accumulation is also referred to as a cultivar with a reduced risk of accumulating glycoalkaloids.

Figure 7:
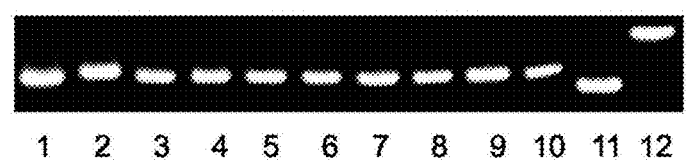
FIG. 7 illustrates the result of performing PCR for the genomic DNA of related species of potato (wild species).

8. Production of Cultivar Having Decreased or Eliminated Glycoalkaloid Accumulation by Crossing It is possible to produce a cultivar having decreased or eliminated glycoalkaloid accumulation using a mutant strain obtained by the above described method or a selected wild-type strain as a mother plant. In a case in which a mutant strain obtained from a cultivar is used as a mother plant, it is considered to be advantageous that crossing the mutant strains with each other or crossing the mutant strains having a mutation of the same target gene at different sites in terms of early fixation of mutation. A disorder such as incompatibility according to the classic self-incompatibility and the endosperm balance number (EBN) theory with regard to the crossing with potato or a related species of potato is known, but these can be subjected to crossing or treatment equivalent thereto by performing treatment such as direct pollination to the ovule, ovule culture, implementation of normal and reciprocal crossing, and somatic cell hybridization. For these, it is possible to refer to "Potato Dictionary" (2012) edited by Japan Root and Tuber Crops Development Association Inc. Foundation, Zenkoku Noson Kyoiku Kyokai Co., Ltd., and "Handbook of potato production, improvement, and postharvest management" (2006) edited by Gopal and Paul Khurana p. 77-108 Haworth Press Inc. In a case in which a wild-type strain is the introduction source having a gene with a mutation, a gene having a mutation can be introduced by setting the parent (the introduction destination) as the cultivated species and performing backcrossing with the parent while maintaining the taste and the excellent cultivation characteristics of the cultivated species. In addition, a genetic marker related to a mutation can be acquired by analyzing the site mutated in the gene at the nucleotide sequence level. Moreover, plural genetic markers positioned in the vicinity of the gene can be acquired, and the screening of the progeny in which mutation is introduced at only desired mutation sites can also be efficiently performed by referring to the genome information such as the potato genome sequence (Nature, 2011; 475: 189-95) reported last year. It is possible to introduce only a necessary part (gene region) from the introduction source to the introduction destination if detailed markers are acquired not only in the vicinity of the gene but also in the region covering the entire genome. In this case, there is a possibility that the separation between the marker and the trait occurs at a certain probability if there is a genetic distance between the marker and the gene (trait) to be introduced, and thus the assay of the trait is essential. However, since the genetic mutation found in the present invention is consistent with the trait, the assay of trait is not required, and a reliable assay of the crossed seed can be performed at the time when the seed germinates and the DNA thereof is obtained. The assay technique using these DNA markers can be performed by referring to "Genetic analysis at genome level: MAP and QTL" Ukai Yasuo (2001) University of Tokyo Press, or the like. For example, the presence of the DNA markers can be determined using a polynucleotide such as a primer. Examples of primers to be used herein include a primer containing a sequence that comprises the sequences set forth in SEQ ID NO: 23 and SEQ ID NO: 24, respectively, a primer containing a sequence that comprises the sequence set forth in SEQ ID NO: 25 and the sequence set forth in SEQ ID NO: 26, and a primer containing a partial sequence thereof. If a sequence that is a genetic marker is presented, mutant individuals can be easily selected by examining if the relevant sequence is contained in the genomic DNA. For example, the following method can be employed. DNA is extracted from each individual containing no mutation and each individual containing a mutation. A general PCR method is performed using such DNA as a template and primers set for a region containing a mutation and set for the peripheral region. No DNA fragment is amplified in the case of DNA obtained from individuals containing no mutation. In the case of DNA obtained from individuals containing mutation, a specific amplified DNA fragment is obtained. Also, the relevant sequence can also be detected by subjecting the genomic DNA to Southern hybridization method using a genetic marker sequence as a probe. In this manner, mutant individuals can be selected using a genetic marker. Furthermore, only a sequence set with only the peripheral region without directly using inserted sequence that is a mutation, can be used as a genetic marker. For example, FIG. 7 shows the results of performing PCR for the genomic DNA using a primer on the $4^{th}$ exon, U900+:TTAACAG-GAGGAACAAGAGG (SEQ ID NO: 20) and a primer on the $6^{th}$ exon, U926: AATGCCTGGCTTAGTTTCAA (SEQ ID NO: 21). The increased size of the DNA fragment was detected in individuals containing the mutation, compared with the DNA fragment amplified in the control Sassy. Screening of progeny individuals using a PCR method or the like can also be performed for seedlings having budded from seeds resulting from crossing.

EXAMPLES

Hereinafter, the present invention will be described in more detail with reference to Examples, but the present invention is not limited thereto.

Example 1

Acquisition of Full-Length Sequence of Glycoalkaloid Biosynthesis Gene E mRNA was extracted from the sprouts of the potato (*Solanum tuberosum*) variety "Sassy" (sold by Japan Agribio Company) using RNeasy (QIAGEN). Total cDNA was synthesized using SuperScript First-Strand System (Invitrogen). An aglycone of glycoalkaloids is said to be made of cholesterol, but there is no definitive evidence to indicate it (Non-patent literature 1). However, even when an aglycone is assumed to be produced from a related compound, some oxidation processes are still required therefor. At least the following 3 types of enzyme, cytochrome P450 monooxygenase, dioxygenase, and NADPH-flavin reductase may be involved in the oxidation processes. Of them, P450 monooxygenase was considered to be a target, and attention was given to TC155233 gene, for which many EST clones had been isolated from sprouts, based on the disclosed information, DFCI Potato Gene Index (http://compbio.dfci.harvard.edu/tgi/plant.html) Release 11.0, as a gene to be expressed by potato.

PCR was performed based on this sequence (conditions: 95° C. for 5 minutes, 30 cycles of 95° C. for 30 seconds, 55° C. for 30 seconds, and 72° C. for 3 minutes, followed by 72° C. for 10 minutes) using primers [U890: GAG-GCTAAGAAAAAGAGAGAGAGA (SEQ ID NO: 6) and U889: CGTTCTACAAAAACATCCAATTT (SEQ ID NO: 7)]. The amplification product was cloned using a TOPOTA Cloning Kit for sequencing (Invitrogen). Furthermore, the nucleotide sequence was determined using ABI310 (Applied Biosystems). The part including ORF is set forth in SEQ ID NO: 2 and the amino acid sequence of the enzyme encoded from the cDNA sequence is set forth in SEQ ID NO: 1.

Figure 3:
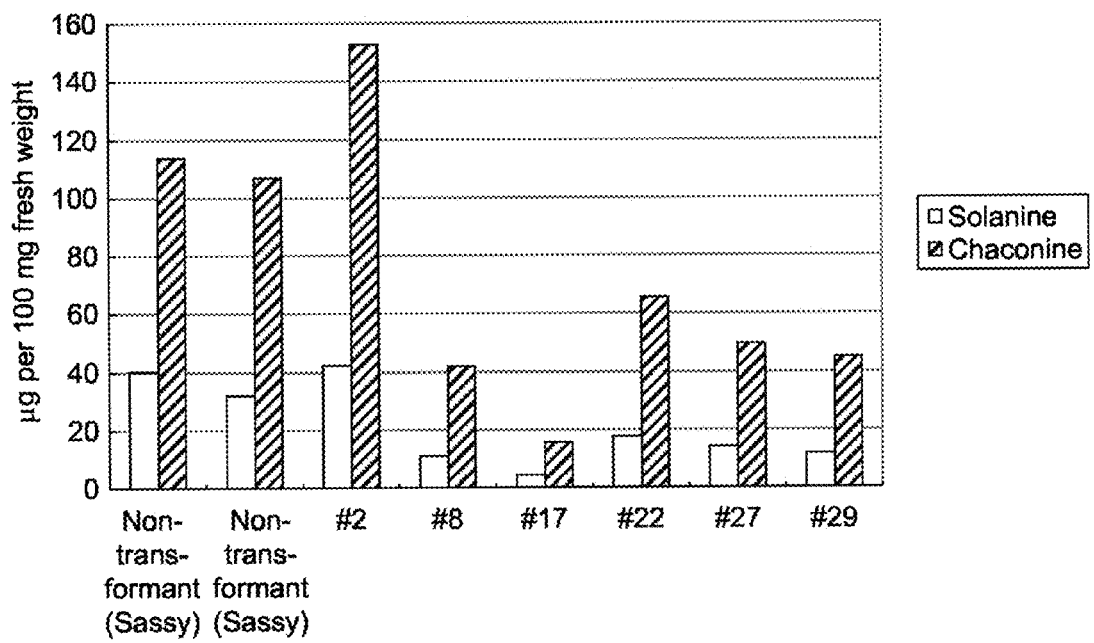

Meanwhile, the homologous gene of tomato corresponds to SGN-U583521 in the Solanaceae Genome Network (http://solgenomics.net/index.pl). The part including ORF is set forth in SEQ ID NO: 4, and the amino acid sequence of the enzyme encoded from the cDNA sequence is set forth in SEQ ID NO: 3. The nucleotide sequences of the genes exhibited homology of 95% when compared with each other. The genomic structure of the genome sequence of the tomato homologous gene is also listed in the Solanaceae Genome Network as SL1.00sc03540, and it has been reported that the genome sequence of the tomato gene includes 7 introns. However, the function thereof is not reported at all in the website (FIG. 1-1 to FIG. 1-3).

Example 2

Isolation of Genomic Gene of Glycoalkaloid Biosynthetic Gene E

Genomic DNA was extracted from "Sassy" using DNeasy (QIAGEN). PCR was performed using the same primers as in Example 1, U904 (TGATAAGGAAATCCTGGGAGA (SEQ ID NO: 8) and U901 (AGAGAAGCCAT-GAAGGATGG (SEQ ID NO: 9)). PCR was further performed for the $2^{nd}$ intron using as an enzyme PrimeSTAR HS DNA Polymerase (TAKARA BIO INC.) and primers (U898: GAAATACGCTACTACGGAAGAACC (SEQ ID NO: 10) and U899: CGTCATTTGCCTAATCTCATC (SEQ ID NO: 11)). Thus, the nucleotide sequence of the full-length genomic DNA was determined (SEQ ID NO: 5). It was revealed that introns were present at 7 positions.

The genome sequence of the potato gene (Xu et al., Nature (2011) 475: 189-197) has been recently reported. The genome sequence is open to the public in HP (http://potatogenomics.plantbiology.msu.edu/index.html) of the Potato Genome Sequencing Consortium Data Release. It is possible to determine the genome of the gene E based on this sequence. The genome sequence of the tomato gene is also listed in the Solanaceae Genome Network (http://solgenomics.net/index.pl), and it has been reported that the genome sequence of the tomato gene includes 7 introns. However, the function thereof is not reported at all in the website.

Example 3

Construction of Vector for Creating Suppression Transformant of Glycoalkaloid Biosynthesis Gene E As a method of suppressing the gene by transformation, the expression (commonly referred to as the RNAi method in plants) of the complementary strand gene fragment in the reverse direction having a structure driven by a strong promoter was performed [Chuang and Meyerowitz, Proc. Natl. Acad. Sci. U.S.A., 97, 4985-90 (2000), and Wesley et al., Plant J., 27, 581-90 (2001)]. PCR (conditions: 95° C. for 5 minutes, 30 cycles of 95° C. for 30 seconds, 55° C. for 30 seconds, and 72° C. for 30 seconds, followed by 72° C. for 10 minutes) was performed for the full-length cDNA obtained in Example 1 using primers [U675: GAGCTCTA-GAGGTTTGGGACAGGAGGAAT (SEQ ID NO: 12) and U676: GGATCCATATGCAAGCCTGTGCATCTTAT (SEQ ID NO: 13)], thereby obtaining a gene fragment. The pKT230 vector for plant transformation (FIG. 2) was constructed by ligating the 35S RNA promoter of cauliflower mosaic virus, the gene fragment in the forward direction, the $3^{rd}$ intron of *Arabidopsis thaliana* phytoene desaturase gene (AT4g14210), the gene fragment in the reverse direction, and a terminator of a nopaline synthase gene in this order based on the pKT11 binary vector (JP Patent Publication (Kokai) No. 2001-161373 A).

Example 4

Production of Transgenic Plant of Potato

The vector prepared in Example 3 was introduced into *Agrobacterium tumefaciens* GV3110 strain by an electroporation method (Plant Molecular Biology Manual, C2, 1-32 (1994) edited by Gelvin and Schilperoor, Kluwer Academic Publishers). The *Agrobacterium tumefaciens* GV3110 strain containing the vector was subjected to a shake culture at 28° C. for 12 hours in a YEB liquid medium [5 g/l beef extract, 1 g/l yeast extract, 5 g/l peptone, 5 g/l sucrose, and 2 mM magnesium sulfate (pH7.2)] containing 50 ppm kanamycin. The culture solution of 1.5 ml was centrifuged at 10,000 rpm for 3 minutes to harvest, and then the resultant was washed with an LB medium of 1 ml to remove kanamycin. The culture solution was further centrifuged at 10,000 rpm for 3 minutes to harvest, and then resuspended in an MS medium [Murashige & Skoog, Physiol. Plant., 15, 473-497 (1962)] containing 3% sucrose of 1.5 ml, thereby obtaining a bacterial solution for infection.

The transformation of potato was carried out according to [Monma (1990) Plant tissue culture 7: 57-63]. The microtuber obtained from "Sassy" of a potato variety was sliced into 2 to 3 mm, and used as the material for *Agrobacterium* infection. This was immersed in the bacterial solution of *Agrobacterium* described above, and then placed on sterilized filter paper to remove the excess *Agrobacterium*. The resultant was placed on an MS medium (including 1 ppm zeatin, 0.1 ppm IAA, 100 μM acetosyringone, and 0.8% agar) in a Petri dish, and cultured at 25° C. for 3 days under the conditions of lighting for 16 hours (photon flux density 32 μE/m$^2$ s) and without lighting for 8 hours. Subsequently, the resultant was cultured for 1 week in a medium containing 250 ppm carbenicillin instead of acetosyringone. Thereafter, the resultant was further transferred on a medium containing 50 ppm kanamycin and was subcultured every 2 weeks. Adventitious buds were formed during this time, and shoots were generated. Shoots that had grown were placed on an MS medium containing 250 ppm carbenicillin and 100 ppm kanamycin, but not containing any plant growth regulating substance. The rooted shoots were subjected to PCR (conditions: 95° C. for 5 minutes, 30 cycles of 95° C. for 30 seconds, 55° C. for 30 seconds, and 72° C. for 1 minute, followed by 72° C. for 10 minutes), so that the individuals containing the kanamycin resistant gene as a foreign gene were detected from among the grown kanamycin resistant plant bodies. It was thus confirmed that the redifferentiated plant was a transgenic plant. Here, as a primer for specific amplification of the sequence of the kanamycin resistant gene, TAAAGCACGAGGAAGCGGT (SEQ ID NO: 14) and GCACAACAGACAATCGGCT (SEQ ID NO: 15) were used. As described above, 30 lineages of transgenic plant bodies of potato into which the pKT230 vector had been introduced were acquired.

Example 5

Glycoalkaloid Content of Transgenic Plant and Expression Analysis of Gene E

Glycoalkaloid contents were measured by the following method (JP Patent Publication No. 2011-27429) using liquid chromatography using an alkali resistant reverse phase chromatography column.

In vitro stems of 30 individuals obtained in Example 4 were allowed to grow for one month after subculturing, and 2 to 4 pieces thereof each were collected together to be about 100 mg, and 990 μL of 0.1% formic acid in 80% MeOH aq. and 10 μg/10 μL of brassinolide (Brassino Co., Ltd.) as an internal standard were added thereto, and then the resultant was crushed using a mixer mill (⅕s sec, 10 min, and 4° C.). The debris thus obtained was subjected to centrifugation (10,000 rpm, 5 min, and 4° C.) to perform alcohol precipitation. The supernatant of 25 μL was separated from the resultant, a 0.1% formic acid aqueous solution of 475 μL was added thereto, the resultant was filtered through Multiscreen Solvinert (Merck Millipore), and then the filtrate was analyzed using LC-MS (LCMS-2010EV (Shimadzu Corporation) or Alliance e2795 Q-micro (WATERS)). The separation and the analysis were performed under the conditions of LC of a column (XBridge™ Shield RP18-5 (φ2.1×150 mm (WATERS)) and an isocratic (column oven: 40° C.) mobile phase (A: 10 mM aqueous solution of ammonium bicarbonate (pH 10): B: acetonitrile=40:60). The quantification was performed using a standard (chaconine and solanine (both manufactured by Sigma-Aldrich Co., LLC.).

Figure 4:
FIG. 4 illustrates the result of performing RT-PCR for RNA extracted from the in vitro stems of potato transformants.

The degree of glycoalkaloid accumulation was low with favorable reproducibility in five lineages (#8, #17, #22, #27, and #29) of 30 individuals thus obtained. Hence, the in vitro stems of one lineage (#2) in which the glycoalkaloid content was not low, and two control individuals into which no gene had been introduced, were ground in liquid nitrogen. Thereafter, a half of the resultant was subjected to the measurement of glycoalkaloid contents and the other half thereof was subjected to the extraction of mRNA using RNeasy (QIAGEN). Entire cDNA synthesis was performed using SuperScript First-Strand System (Invitrogen). These individuals exhibited extremely lower glycoalkaloid accumulation than that of nontransgenic plants (2 individuals) (FIG. 3). As a result of further RT-PCR using primers [U887: TAAGGGACTCAAGGCTCGAA (SEQ ID NO: 16), and U886: TTCCTCTTTGGCTTTCTCCA (SEQ ID NO:17)] (conditions: 95° C. for 5 minutes, 25 cycles of 95° C. for 30 seconds, 55° C. for 30 seconds, and 72° C. for 3 minutes, followed by 72° C. for 5 minutes), mRNA expression was observed at extremely low levels or could not observed in all individuals (FIG. 4). From this fact, it was verified that glycoalkaloid accumulation is extremely reduced by suppressing the expression of the gene E, and the gene E is a gene that encodes a glycoalkaloid biosynthetic enzyme. In vitro plants of these 5 lineages were grown together with the non-transformants, and three individuals each were acclimated to commercially available culture soil for vegetables and cultivated according to a conventional method in a biohazard greenhouse, and the tubers were harvested. Each individual of the five lineages (#8, #17, #22, #27, #29) showed growth equivalent to the non-transformants, and tubers equivalent to those of the non-transformants could be harvested (Table 1).

TABLE 1

| Lineage No. | Number of tubers | Standard deviation | Average weight per tuber (g) | Total weight per stock (g) | Standard deviation |
|---|---|---|---|---|---|
| Non-transformant | 15.0 | 3.6 | 17.7 | 260.2 | 35.3 |
| #8 | 21.0 | 6.2 | 14.3 | 291.3 | 39.9 |
| #17 | 19.7 | 3.8 | 15.6 | 297.9 | 17.8 |
| #22 | 18.3 | 3.8 | 18.3 | 321.3 | 37.2 |
| #27 | 24.3 | 4.0 | 15.1 | 360.3 | 16.2 |
| #29 | 19.7 | 4.5 | 19.7 | 268.2 | 50.8 |

Figure 5:
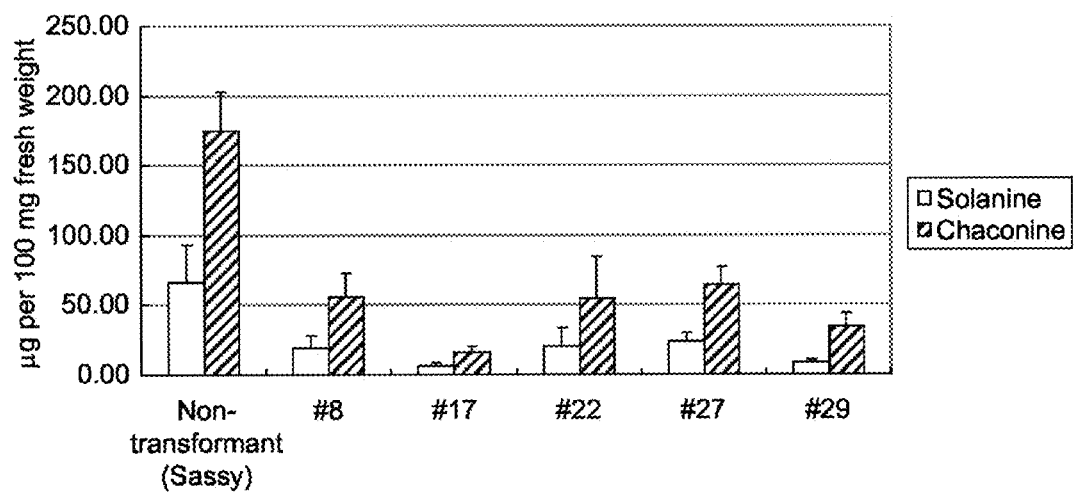
FIG. 5 illustrates the glycoalkaloid contents of the epidermis of the tubers of potato transformants. The error bar indicates the standard deviation.

Moreover, the central epidermis of three tubers each of the plants thus harvested were peeled off by about 1 mm, and the glycoalkaloid content thereof was analyzed in the same manner as above. As a result, it was surprisingly confirmed that the glycoalkaloid content in the tubers was significantly low (FIG. 5).

Example 6

Production of Transgenic Plant of Tomato

Figure 6:
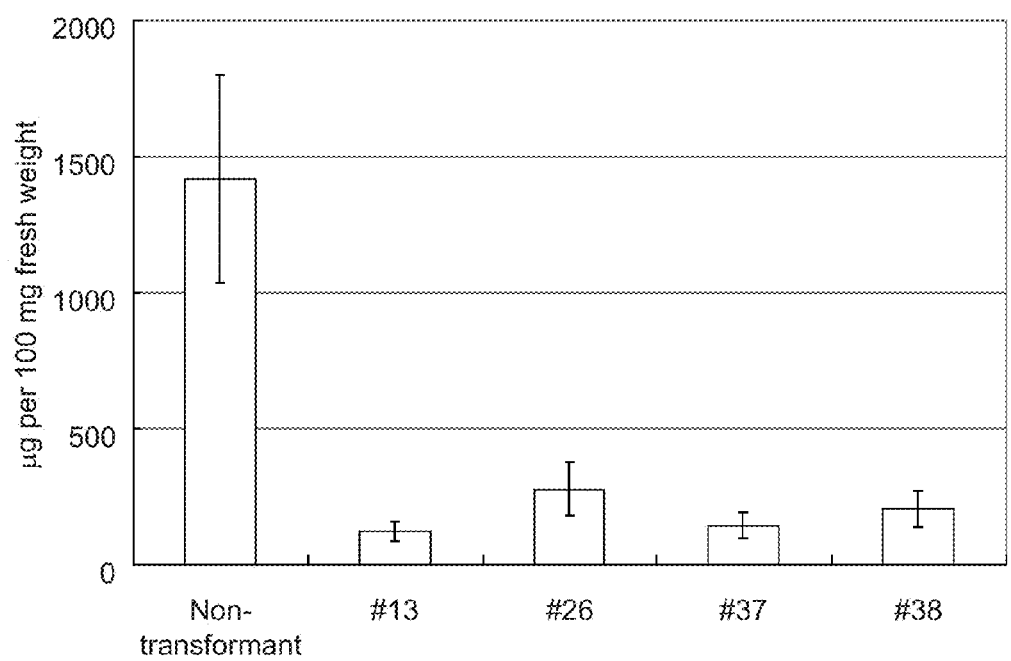
FIG. 6 illustrates the glycoalkaloid contents of the young leaves of tomato transformants. The error bar indicates the standard deviation.

Tomato was transformed according to [Sun et al., (2006) Plant Cell Physiol. 47: 426-431]. An *Agrobacterium tumefaciens* AGL0 strain containing the pKT230 vector constructed in Example 3 was cultured to use as the bacterial solution for infection. A section of 5 mm or smaller of a cotyledon of each sterile seeded plant of the "Microtom" tomato (*Solanum lycopersicum*) experimental lineage was immersed in the *Agrobacterium* suspension described above and infected for 10 minutes, and then the leaf was placed on sterilized filter paper to remove excess *Agrobacterium*. The leaf was placed on a coexistent MS medium (including 1.5 mg/l zeatin, 40 µM acetosyringone, and 0.3% gelrite) [Murashige & Skoog, Physiol. Plant., 15, 473-497 (1962)] in a Petri dish, and then culture was performed at 25° C. for 3 days in a dark place. The section was subcultured every two weeks in a selective MS medium 1 (including 1.5 mg/l zeatin, 100 mg/l kanamycin, 375 mg/l Augmentin and 0.3% gelrite) at 25° C. under the conditions of lighting for 16 hours (photon flux density 32 µE/m$^2$ s) and without lighting for 8 hours. Adventitious buds were formed during this time, and shoots were generated. For further growth of shoots, a leaf was transplanted to a selective MS medium 2 (including 1.0 mg/l zeatin, 100 mg/l kanamycin, 375 mg/l Augmentin, and 0.3% gelrite), and shoots that had grown were rooted in a selective MS medium of ½ concentration (including 100 mg/l kanamycin, 375 mg/l Augmentin, and 0.3% gelrite). The shoots were subjected to PCR (conditions: 95° C. for 5 minutes, 30 cycles of 95° C. for 30 seconds, 55° C. for 30 seconds, and 72° C. for 1 minute, followed by 72° C. for 10 minutes) so that individuals containing the kanamycin resistant gene as a foreign gene were detected from among the grown kanamycin resistant plant bodies. It was thus confirmed that the redifferentiated plant was a transgenic plant. Here, TAAAGCACGAGGAAGCGGT (SEQ ID NO: 18) and GCACAACAGACAATCGGCT (SEQ ID NO: 19) were used as primers for specific amplification of the sequence of the kanamycin resistant gene. As described above, 13 lineages of transgenic plant bodies of tomato into which the pKT230 vector had been introduced were acquired. The 13 individuals thus obtained were acclimated to a greenhouse and cultivated for about one month, and then about 100 mg each of newly developed three young leaves was weighed and the glycoalkaloid content thereof was measured by the method of Example 5 (using liquid chromatography using an alkali resistant reverse phase chromatography column) in the same manner as potato. Provided that, analysis conditions employed herein for the above sample solvent are isocratic conditions comprising the proportion of mobile phase A: 10 mM aqueous solution of ammonium bicarbonate (pH 10): mobile phase B (MeCN)=60:40. The tomatine content of 4 lineages among the 13 lineages was significantly as low as 280 µg (or less) per 100 mg of fresh weight, which was ⅕ or less that of the control (FIG. 6).

Example 7

Screening of Plant Having Mutated Glycoalkaloid Biosynthetic Gene E

Self-fertilized seeds of the variety "Hokkaikogane" are subjected to mutation treatment by quantum beam irradiation (NIRS-HIMAC irradiation device (RADIATION RESEARCH 154, 485-496 (2000)) with a 90 to 470 Gy neon ion beam at 30 kev/µm, a 125 to 250 Gy argon ion beam at 89 kev/µm, or a 40 to 80 Gy iron ion beam at 185 kev/µm). After the mutation treatment, the terminal buds of plant bodies that have grown after sowing are pruned back. After pruning back, the axillary buds of leaves are grown, leaves that have developed from the axillary buds are collected, and their genomic DNA is extracted by a conventional method. PCR is performed using the genomic DNA as a template and the following primers [U890: GAGGCTAAGAAAAAGA-GAGAGAGA (SEQ ID NO: 6), U889: CGTTCTA-CAAAAACATCCAATTT (SEQ ID NO: 7), U904: TGA-TAAGGAAATCCTGGGAGA (SEQ ID NO: 8), and U901: AGAGAAGCCATGAAGGATGG (SEQ ID NO: 9)). To amplify the 2$^{nd}$ intron, PCR was performed for a structural gene using PrimeSTAR HS DNA Polymerase (TAKARA BIO INC.) as the enzyme and primers (U898: GAAATACGCTACTACGGAAGAACC (SEQ ID NO: 10) and U899: CGTCATTTGCCTAATCTCATC (SEQ ID NO: 11)). Thus, the region containing the gene E is acquired and cloning is further performed using a kit for gene cloning or the like. The nucleotide sequence of the region cloned is determined, whereby an individual with a mutation in the gene E can be selected.

Example 8

Identification of Plant Having Mutated Glycoalkaloid Biosynthetic Gene E

Figure 9:
FIG. 9 illustrates the results of performing RT-PCR for RNA extracted from in vitro plant bodies of related species of potato (wild species).

The plant bodies of ten lineages (FTT1, FTT2, FTT3, FTT4, FTT5, FTT6, FTT7, FTT8, FTT10, and FTT11) were obtained by germinating the true seeds of PI 210040, PI 310946, PI 283079, PI 458380, PI 498254, PI 498255, PI 498256, PI 365332, PI 310944, and PI 310945, which belong to the *Solanum marinasense* that is a related species of a wild species of potato (*Solanum tuberosum*) obtained from the NRSP-6-United States Potato Genebank (http://www.ars-grin.gov/nr6/). The plant bodies of one lineage (FTT16) were obtained by germinating the true seeds of PI473351 which belongs to *Solanum lignicaule*. The extraction of the genomic DNA from these lineages was performed using DNeasy (QIAGEN). The extraction of RNA was performed using RNeasy (QIAGEN), and the synthesis of the entire cDNA was performed using SuperScript First-Strand System (Invitrogen). PCR (conditions: 95° C. for 5 minutes, 30 cycles of 95° C. for 30 seconds, 55° C. for 30 seconds, and 72° C. for 3 minutes, followed by 72° C. for 5 minutes) was performed for genomic DNA (the control was the genomic DNA of the variety, "Sassy") using the U900+ primer: TTAACAGGAGGAACAAGAGG (SEQ ID NO: 20) on the 4$^{th}$ exon and the U926 primer: AATGCCTGGCT-TAGTTTCAA (SEQ ID NO: 21) on an exon. As a result, an insertion of about 500 bases was confirmed in FTT1, FTT2, FTT3, FTT4, FTT5, FTT6, FTT7, FTT8, FTT10, and FTT11 and an insertion of about 900 bases was confirmed in FTT16, as compared with the genome sequence of the control variety "Sassy" (FIG. 7). The amplified DNA was directly subjected to a sequencing reaction using the U900+ primer and a primer on an exon, U1035: CATCCCATCTT-GAAGGATTAAA (SEQ ID NO: 22). The inserted regions and the partial nucleotide sequence of the insertion sequence were compared with the genome sequence of the variety, "Sassy" (FIG. 8). The insertion sequence was located at the same position (within the 4$^{th}$ intron) for all 3 lineages. Furthermore, the conserved 5' splicing sequence of the 4$^{th}$ intron was not GT, but was GC, for FTT1 and FTT2. It was thus inferred that normal splicing could not take place. Furthermore, RT-PCR (conditions: 95° C. for 5 minutes, 30 cycles of 95° C. for 30 seconds, 55° C. for 30 seconds, and 72° C. for 3 minutes, followed by 72° C. for 5 minutes) was performed for cDNA using the primers on the 2$^{nd}$ exon, U925 and U1035. The amount of the transcription product detected in normal potatoes was extremely low for FTT1 and FTT16 (FIG. 9). The 5'-terminal sequence in the sequence inserted in FTT1 is set forth in SEQ ID NO: 23, and the 3'-terminal sequence in the sequence inserted in the same is set forth in SEQ ID NO: 24. In addition, the 5'-terminal sequence in the sequence inserted in FTT16 is set forth in SEQ ID NO: 24, and the 3'-terminal sequence in the sequence inserted in the same is set forth in SEQ ID NO: 26. The sequence between the sequence set forth in SEQ ID NO: 23 and the sequence set forth in SEQ ID NO: 24 remains undetermined, and the sequence between the sequence set forth in SEQ ID NO: 25 and the sequence set forth in SEQ ID NO: 26 remains undertermined. These are omitted in FIG. 8. Because of the sequence insertion, it was confirmed that normal transcription products were not produced and the gene was disrupted. It was thus revealed that PI 210040, PI 310946, PI 283079, PI 458380, PI 498254, PI 498255, PI 498256, PI 365332, PI 310944, and PI 310945, which belong to *Solanum marinasense*, and PI473351, which belongs to *Solanum lignicaule*, were mutant plants containing the mutated gene E.

The glycoalkaloid contents of in vitro stems of the plant bodies of FTT1, FTT2, FTT8, and FTT16 were measured by the method described in Example 5. As a result, it was verified that the plant bodies contained no glycoalkaloids including chaconine, solanine, and tomatine.

*Solanum marinasense* is included in the Tuberaosa series (classification of "series" in plant classification), the same series as a normal potato *Solanum tuberosum* according to the literature (C. M Ochoa, 'The Potatoes of South America: Peru, Part I. The Wild Species,' 2004, International Potato Center, Peru). On the other hand, *Solanum lignicaule* belongs to the Ligunicaulia series differing therefrom, but the details thereof are unknown. Both species belong to the same EBN2 group based on the endosperm balance number (EBN) theory ("Handbook of potato production, improvement, and postharvest management" (2006) edited by Gopal and Paul Khurana, p. 77-108, Haworth Press Inc.), and crossing between them is possible. From these facts, it was verified that the finding of a mutant gene using the sequence of the present gene is easy, and the mutated gene E found in *Solanum marinasense* and *Solanum lignicaule* can be used for industrial breeding applications.

Example 9

Production of Cultivar by Crossing

The *Solanum marinasense* PI 210040-derived seed lineage FTT1 used in Example 8 is a diploid. The F1 generation is produced by crossing this FTT1 with 97H32-6 (Phumichi et al., Genome (2005) 48: 977-984) of a diploid potato with a self-incompatibility inhibitor gene. A quarter (¼) of the F2 plants (produced by crossing the F1 plants) that can be obtained herein have the properties of a diploid potato, but contain no glycoalkaloids. A tetraploid potato can be obtained by subjecting the FTT1 itself or the F2 plants lacking glycoalkaloids to doubling treatment using a chemical agent such as colchicine. A novel F1 generation can be obtained by crossing this tetraploid potato with Hokkaikogane, which is a tetraploid and of the general variety. It can be expected that tetraploid potatoes containing no glycoalkaloids can be obtained from ⅟₃₆ of the F2 plants (obtained by crossing the F1 plants). It is unnecessary to measure the glycoalkaloid content for the assay. It is possible to assay the potato by acquiring DNA from the seedling and examining the information of DNA obtained in Example 8, specifically, performing PCR using primers, U900+(SEQ ID NO: 20) on the 4$^{th}$ exon and U926 (SEQ ID NO: 21) on the 6$^{th}$ exon (peripheral regions), and examining the presence or absence of the insertion of about 500 bases via comparison with the amplified fragment from a normal potato.

INDUSTRIAL APPLICABILITY

According to the method of the present invention, a solanaceous plant variety such as potato, in which glycoalkaloids are not accumulated within plant bodies, can be obtained.

All of the publications, patents, and patent applications cited in the present specification shall be incorporated herein by reference in their entirety.

Sequence Listing Free Text

SEQ ID NOS: 6-22 Primer

The invention claimed is:

1. A method of producing a potato plant containing no glycoalkaloids, which comprises:
   (i) obtaining progeny plants by crossing a plant as a mother plant, in which the expression of an oxidase gene involved in glycoalkaloid biosynthesis is suppressed such that glycoalkaloids are not produced;
   (ii) screening for the progeny plants, in which the expression of an oxidase gene involved in glycoalkaloid biosynthesis is suppressed such that glycoalkaloids are not produced; and
   (iii) selecting the progeny plant containing no glycoalkaloids, wherein the mother plant is a plant containing an insertion sequence that comprises the sequences set forth in SEQ ID NO: 23 and SEQ ID NO: 24 in the 4$^{th}$ intron of the oxidase gene, an insertion sequence that comprises the sequence set forth in SEQ ID NO: 25 and the sequence set forth in SEQ ID NO: 26, or an insertion sequence consisting of a partial sequence thereof.

* * * * *